(12) United States Patent
Haque

(10) Patent No.: US 10,405,811 B2
(45) Date of Patent: Sep. 10, 2019

(54) IMAGE PROCESSING METHOD AND APPARATUS, AND PROGRAM

(71) Applicant: General Electric Company, Schenectady, NY (US)

(72) Inventor: Hasnine Haque, Hino (JP)

(73) Assignee: General Electric Company, Schenectady, NY (US)

( * ) Notice: Subject to any disclaimer, the term of this patent is extended or adjusted under 35 U.S.C. 154(b) by 159 days.

(21) Appl. No.: 15/507,166

(22) PCT Filed: Aug. 28, 2015

(86) PCT No.: PCT/US2015/047471
§ 371 (c)(1),
(2) Date: Feb. 27, 2017

(87) PCT Pub. No.: WO2016/033485
PCT Pub. Date: Mar. 3, 2016

(65) Prior Publication Data
US 2017/0273641 A1    Sep. 28, 2017

(30) Foreign Application Priority Data
Aug. 28, 2014 (JP) ................. 2014-173996

(51) Int. Cl.
*A61B 6/00* (2006.01)
*A61B 6/03* (2006.01)
*G01N 15/14* (2006.01)

(52) U.S. Cl.
CPC ............. *A61B 6/03* (2013.01); *A61B 6/504* (2013.01); *A61B 6/5211* (2013.01);
(Continued)

(58) Field of Classification Search
CPC .............................. A61B 6/504; A61B 6/5247
See application file for complete search history.

(56) References Cited

U.S. PATENT DOCUMENTS 5,189,369 A * 2/1993 Takane ................. G01R 33/563
324/306
8,170,328 B2 * 5/2012 Masumoto .............. G06T 19/00
382/128
(Continued)

FOREIGN PATENT DOCUMENTS

JP 2008-259702 A 10/2008
JP 2009-112468 A 5/2009
(Continued)

OTHER PUBLICATIONS

English Translation of the Notice of Allowance for Application No. 2014-173996, dated Jan. 5, 2018.
(Continued)

*Primary Examiner* — Gandhi Thirugnanam

(57) ABSTRACT

Method and apparatus are used to display a slice of tomographic image in a three-dimensional (3D) medical image, for the purpose of achieving better recognition of a vascular structure contained in the slice without degrading spatial resolution of the slice. An example method includes identifying a slice of interest in a 3D medical image representing an anatomical part including a blood vessel; and projecting along a slice axis direction orthogonal to the slice of interest for a region in the 3D medical image including the slice and wider than the slice.

15 Claims, 17 Drawing Sheets

(52) U.S. Cl.
CPC .......... *A61B 6/5223* (2013.01); *A61B 6/5247* (2013.01); *G01N 15/1475* (2013.01); *G01N 2015/1472* (2013.01)

(56) References Cited

U.S. PATENT DOCUMENTS

| | | | | |
|---|---|---|---|---|
| 2004/0175025 | A1* | 9/2004 | Knoplioch | G06T 15/08 382/132 |
| 2006/0233430 | A1* | 10/2006 | Kimura | G06T 7/30 382/128 |
| 2008/0219537 | A1* | 9/2008 | Matsue | G06T 15/08 382/131 |
| 2009/0262896 | A1* | 10/2009 | Maschke | A61B 6/467 378/98 |
| 2010/0104168 | A1* | 4/2010 | Dobbe | A61B 5/02007 382/134 |
| 2011/0103658 | A1* | 5/2011 | Davis | G01N 21/4795 382/128 |
| 2012/0121147 | A1* | 5/2012 | Huang | G06T 7/32 382/131 |
| 2012/0310092 | A1* | 12/2012 | Yawata | A61B 8/00 600/443 |
| 2014/0147025 | A1* | 5/2014 | Periaswamy | A61B 6/025 382/131 |
| 2017/0273641 | A1* | 9/2017 | Haque | A61B 6/03 |

FOREIGN PATENT DOCUMENTS

| | | |
|---|---|---|
| JP | 2012075794 A | 4/2012 |
| JP | 2013-154127 A | 8/2013 |
| JP | 2014-087671 A | 5/2014 |
| JP | 2014151084 A | 8/2014 |

OTHER PUBLICATIONS

International Search Report and Written Opinion for International Application No. PCT/US15/047471, dated Dec. 11, 2015, 11 pages.
English Translation of the JP OA for Application No. 2014-173996. Office Action dated May 9, 2017.

* cited by examiner (a)　　　　　(b)　　　　　(c)

(a)

(b)

(a)

(b)          (c)

TOMOGRAPHIC IMAGE
OF SLICE IN
CONTRAST-ENHANCED
3D CT IMAGE (a)

TOMOGRAPHIC IMAGE
OF SLICE IN
CONTRAST-ENHANCED
3D MR IMAGE (b)

PROJECTION IMAGE OF WIDER-SLICE REGION IN CONTRAST-ENHANCED 3D CT IMAGE (a)

PROJECTION IMAGE OF WIDER-SLICE REGION IN CONTRAST-ENHANCED 3D MR IMAGE (b)

| TOMOGRAPHIC IMAGE OF SLICE IN 3D US IMAGE | PROJECTION IMAGE OF WIDER-SLICE REGION IN 3D US IMAGE | PROJECTION IMAGE OF WIDER-SLICE REGION IN 3D MR IMAGE |
|---|---|---|
|  |  |  |
| (a) | (b) | (c) |

(a)                    (b)

(a)                      (b)

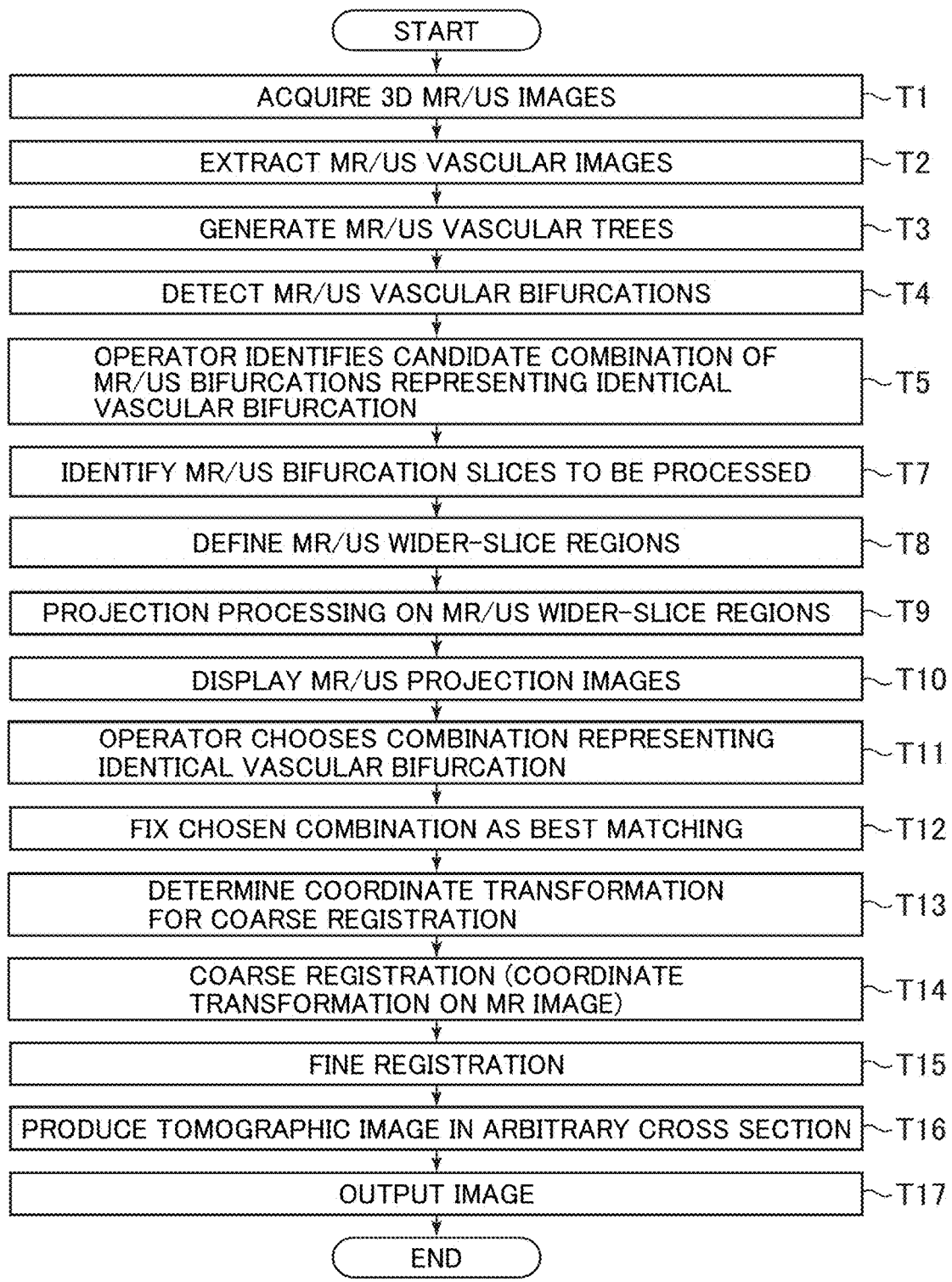

IMAGE PROCESSING METHOD AND APPARATUS, AND PROGRAM

CROSS-REFERENCE TO RELATED APPLICATIONS

This is a national stage application under 35 U.S.C. § 371 (c) of PCT Patent Application No. PCT/US2015/047471, filed on Aug. 28, 2015, which claims priority to Japanese Patent Application No. 2014-173996, filed on Aug. 28, 2014, the disclosures of which are incorporated herein by reference in their entireties.

BACKGROUND

Embodiments of the present invention relate to techniques for displaying tomographic images of a slice in three-dimensional (3D) medical images.

There have been proposed a variety of kinds of image processing using a 3D medical image representing an anatomical part in a subject. Such image processing sometimes require processing of identifying a sice of interest in the 3D medical image, and reconstructing a tomographic image corresponding to the slice for display.

For example, in recent years, a process involving imaging an identical anatomical part in a subject by a plurality of imaging modalities, and presenting a resulting plurality of 3D medical images at the same time for reference has been practiced for the purpose of improving accuracy of image diagnosis. At that time, processing of registering the plurality of 3D medical images to align coordinate systems of the images with each other is generally applied. In registering 3D medical images with each other, for example, an image processing apparatus is arranged to identify, in two 3D medical images to be registered, candidate combinations of slices representing an identical portion of tissue common to the images, and reconstruct tomographic images corresponding to the slices for display. An operator refers to the tomographic images to visually identify a combination of slices possibly representing the identical portion of tissue. The image processing apparatus performs coordinate transformation on the 3D medical images so that tissue structures in the slices in the thus-identified combination positionally fit over each other.

In identifying a slice of interest in a 3D medical image and reconstructing a tomographic image of the slice for display, the slice width of the slice is generally set to a relatively small value, for example, of the order of 0.5 mm in a real space, to improve resolution of the tomographic image and enhance spatial resolution.

The smaller slice width of a slice to be identified, however, reduces information on tissue contained in the slice in a slice width direction, which makes it especially difficult to recognize a vascular structure serving as anatomical landmark. On the other hand, an excessively increased slice width lowers spatial resolution of the slice, which may be sometimes unsuitable for the purpose. Especially when registering 3D images with each other, this is an unfavorable factor leading to deterioration of precision of registration.

Under such circumstances, there is a need for a technique for displaying a tomographic image of a slice in a 3D medical image that allows better recognition of a vascular structure contained in the slice without degrading spatial resolution of the slice.

SUMMARY

The invention in its first aspect provides an image processing method comprising an identifying step of identifying a slice of interest in a three-dimensional (3D) medical image representing an anatomical part including a blood vessel and a projecting step of applying projection processing in a slice axis direction of the slice to pixel values for a region in the 3D medical image including the slice and wider than a slice width of the slice.

The invention in its second aspect provides the image processing method in the first aspect, further comprising a displaying step of displaying a projection image obtained by the projection processing, wherein the identifying step identifies a first slice in a first 3D medical image representing the anatomical part, and a second slice in a second 3D medical image representing the anatomical part, the second slice being likely to contain an identical partial vascular structure to that contained in the first slice, the projecting step applies first projection processing in a slice axis direction of the first slice for a first region in the first 3D medical image including the first slice and wider than the first slice, and applying second projection processing in a slice axis direction of the second slice for a second region in the second 3D medical image including the second slice and wider than the second slice, and the displaying step displays a first projection image obtained by the first projection processing and a second projection image obtained by the second projection processing.

The invention in its third aspect provides the image processing method in the second aspect, wherein the identifying step identifies a slice in the first 3D medical image containing a first vascular bifurcation as the first slice, and identifies a slice in the second 3D medical image containing a second vascular bifurcation likely to be an identical vascular bifurcation to the first one as the second slice.

The invention in its fourth aspect provides the image processing method in the third aspect, further comprising a registering step of registering the first and second 3D medical images with each other so that the first and second vascular bifurcations fit over each other.

The invention in its fifth aspect provides the image processing method in the fourth aspect, wherein the identifying step identifies a plurality of combinations of the first and second vascular bifurcations, the method further comprises a choosing step of choosing one of the plurality of combinations in response to a prespecified operation by an operator, and the registering step registers the first and second 3D medical images with each other so that the first and second vascular bifurcations constituting the chosen combination fit over each other.

The invention in its sixth aspect provides an image processing apparatus comprising identifying section for identifying a slice of interest in a three-dimensional (3D) medical image representing an anatomical part including a blood vessel; projecting section for applying projection processing in a slice axis direction of the slice to pixel values for a region in the 3D medical image including the slice and wider than a slice width of the slice; and displaying section for displaying a projection image obtained by the projection processing.

The invention in its seventh aspect provides the image processing apparatus in the sixth aspect, wherein the identifying section identifies a first slice in a first 3D medical image representing the anatomical part, and a second slice in a second 3D medical image representing the anatomical part, the second slice being likely to contain an identical partial vascular structure to that contained in the first slice, the projecting section applies first projection processing in a slice axis direction of the first slice for a first region in the first 3D medical image including the first slice and wider than the first slice, and applying second projection processing in a slice axis direction of the second slice for a second region in the second 3D medical image including the second slice and wider than the second slice, and the displaying section displays a first projection image obtained by the first projection processing and a second projection image obtained by the second projection processing.

The invention in its eighth aspect provides the image processing apparatus in the seventh aspect, wherein the identifying section identifies a slice in the first 3D medical image containing a first vascular bifurcation as the first slice, and identifies a slice in the second 3D medical image containing a second vascular bifurcation likely to be an identical vascular bifurcation to the first one as the second slice.

The invention in its ninth aspect provides the image processing apparatus in the eighth aspect, further comprising registering section for registering the first and second 3D medical images with each other so that the first and second vascular bifurcations fit over each other.

The invention in its tenth aspect provides the image processing apparatus in the ninth aspect, wherein the identifying section identifies a plurality of combinations of the first and second vascular bifurcations, the apparatus further comprises choosing one of the plurality of combinations in response to a prespecified operation by an operator, and the registering section registers the first and second 3D medical images with each other so that the first and second vascular bifurcations constituting the chosen combination fit over each other.

The invention in its eleventh aspect provides the image processing apparatus in any one of the seventh through tenth aspects, wherein the identifying section identifies a combination of vascular bifurcations for which a degree of similarity higher than a certain level is calculated as the first and second vascular bifurcations.

The invention in its twelfth aspect provides the image processing apparatus in any one of the seventh through tenth aspects, wherein the identifying section identifies a combination of vascular bifurcations specified by the operator as the first and second vascular bifurcations.

The invention in its thirteenth aspect provides the image processing apparatus in any one of the seventh through twelfth aspects, wherein the projecting section applies the projection processing by maximum intensity projection processing, minimum intensity projection processing, or average intensity projection processing.

The invention in its fourteenth aspect provides the image processing apparatus in the thirteenth aspect, wherein the projecting section applies the maximum intensity projection processing to a 3D medical image having higher pixel values corresponding to blood vessels than average pixel values corresponding to other tissue.

The invention in its fifteenth aspect provides the image processing apparatus in the thirteenth aspect, wherein the projecting section applies the minimum intensity projection processing to a 3D medical image having lower pixel values corresponding to blood vessels than average pixel values corresponding to other tissue.

The invention in its sixteenth aspect provides the image processing apparatus in any one of the seventh through fifteenth aspects, wherein the first and second 3D medical images are images by mutually different imaging modalities.

The invention in its seventeenth aspect provides the image processing apparatus in the sixteenth aspect, wherein one of the first and second 3D medical image is an ultrasonic image.

The invention in its eighteenth aspect provides the image processing apparatus in any one of the sixth through seventeenth aspects, wherein the anatomical part is a liver or a lung.

The invention in its nineteenth aspect provides the image processing apparatus in any one of the sixth through eighteenth aspects, wherein a width of the first and second slices is equivalent to a width of 3 mm or smaller in a real space, and a width of the first and second regions is equivalent to a width ranging from 5 mm to 30 mm in the real space.

The invention in its twentieth aspect provides a program for causing a computer to function as the image processing apparatus in any one of the sixth through nineteenth aspects.

According to embodiments of the present invention, the configuration thereof can provide a projection image by projecting pixel values in a region including a slice identified in a 3D medical image and wider than a slice width of the slice in its slice axis direction, so that better recognition of a vascular structure contained in the slice is achieved without degrading spatial resolution of the slice.

BRIEF DESCRIPTION OF THE DRAWINGS

FIG. 20 is a flow chart showing flow of processing in the image processing apparatus in accordance with the fourth embodiment.

DETAILED DESCRIPTION

Now several embodiments of the invention will be described. It should be noted that the invention is not limited to these embodiments.

Image processing apparatuses in accordance with these embodiments are those for registering two 3D medical images representing an identical anatomical part in an identical subject with each other, and then, reconstructing a tomographic image representing an arbitrary slice for display. A technique for registration used herein comprises extracting a blood vessel in each of the two 3D medical images to detect a partial vascular structure such as a vascular bifurcation, identifying an identical partial vascular structure common to the two 3D medical images, and applying coordinate transformation to the 3D medical images so that the structures fit over each other. This technique checks similarity of the shape of partial vascular structures, rather than checking similarity of image shading. Accordingly, the present technique is particularly effective in registration between two images having mutually different correspondences of the kind of material with the pixel value, for example, registration between images from mutually different imaging modalities, or registration between images representing an anatomical part with high deformability such as a liver or a lung. In these embodiments, the technique comprises identifying an identical partial vascular structure common to images to be registered, wherein in order to enhance precision of identification, blood vessels surrounding the partial vascular structure to be compared may be referred to in addition to the partial vascular structure itself. In particular, a region containing the partial vascular structure to be compared and its surroundings are subjected to projection processing, such as maximum or minimum pixel intensity projection, to produce a projection image having enhanced blood vessels in that region and display it. By referring to the projection image, an operator may assess similarity of vascular structures in a wide range containing the partial vascular structure, and decide whether the partial vascular structures to be compared are an identical common partial vascular structure or not with high reliability. The image processing apparatuses may employ a result of the decision to achieve image registration with high precision.

Figure 1:
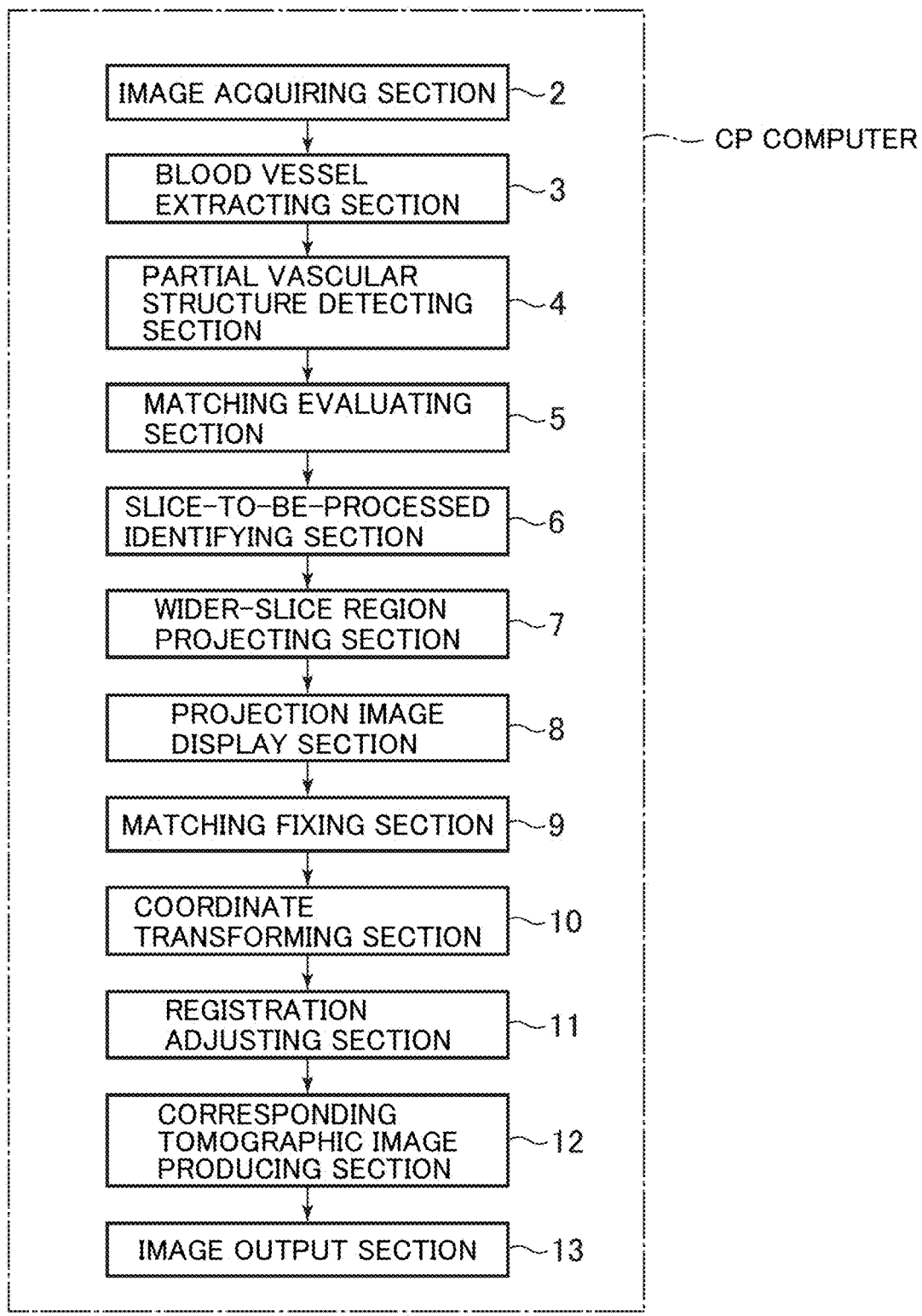
FIG. 1 is a functional block diagram schematically showing a configuration of an image processing apparatus in accordance with a first embodiment.

FIG. 1 is a functional block diagram schematically showing a configuration of an image processing apparatus 1a in accordance with the present embodiment. The image processing apparatus 1a may be implemented by, for example, causing a computer CP to execute a prespecified program.

As shown in FIG. 1, the image processing apparatus 1a comprises an image acquiring section 2, a blood vessel extracting section 3, a partial vascular structure detecting section 4, a matching evaluating section 5, a slice-to-be-processed identifying section 6, a wider-slice region projecting section 7, a projection image display section 8, a matching fixing section 9, a coordinate transforming section 10, a registration adjusting section 11, a corresponding tomographic image producing section 12, and an image output section 13. The slice-to-be-processed identifying section 6, wider-slice region projecting section 7, and projection image display section 8 represent examples of the identifying section, projecting section, and display section, respectively, in the present invention. The matching fixing section 9, coordinate transforming section 10, and registration adjusting section 11 represent an example of the registering section in the present invention.

The image acquiring section 2 acquires two 3D medical images to be registered. It acquires here two input 3D medical images as images to be registered in response to an operation by a user. The image acquiring section 2 defines one of the two 3D medical images as "target image" fixed in registration processing, and the other as "working image" subjected to coordinate transformation in the registration processing. The example here assumes a case in which a 3D MR image $G_{MR}$ and a 3D US image $G_{US}$ representing a liver of an identical subject are acquired as the two 3D medical images to be registered. The 3D US image $G_{US}$ is defined as "target image," and the 3D MR image $G_{MR}$ as "working image." The 3D MR image $G_{MR}$ and 3D US image $G_{US}$ represent examples of the first and second 3D medical images in the present invention.

Figure 2:
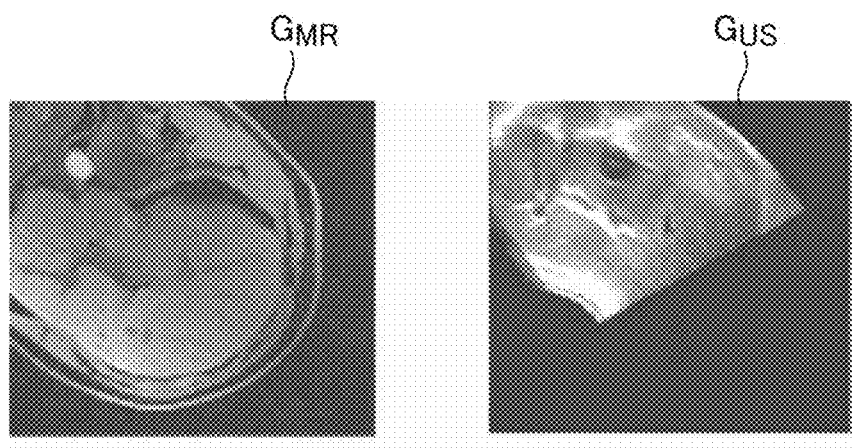
FIG. 2 is a picture showing exemplary 3D MR and US images representing a liver of an identical subject.

FIG. 2 shows exemplary 3D MR image $G_{MR}$ and 3D US image $G_{US}$ representing a liver in an identical subject. It should be noted that the picture shows prespecified tomographic images in the 3D medical images for convenience.

The blood vessel extracting section 3 extracts vascular images representing a blood vessel from the 3D MR image $G_{MR}$ and 3D US image $G_{US}$, respectively. The extraction of the vascular images is achieved using any known technique. For example, a technique disclosed in Non-patent Document: Kirbus C and Quek F, "A review of vessel extraction technique and algorithms," ACM Computer Surveys (CSUR), 36(2), 81-121, 2004, is used. The vascular image in the 3D MR image $G_{MR}$ will be referred to hereinbelow as MR vascular image $V_{MR}$, and that in the 3D US image $G_{US}$ as US vascular image $V_{US}$. In the example here, an image representing a hepatic portal vein or a hepatic vein is extracted as the vascular image. The vascular image is extracted as binarized image.

Figure 3:
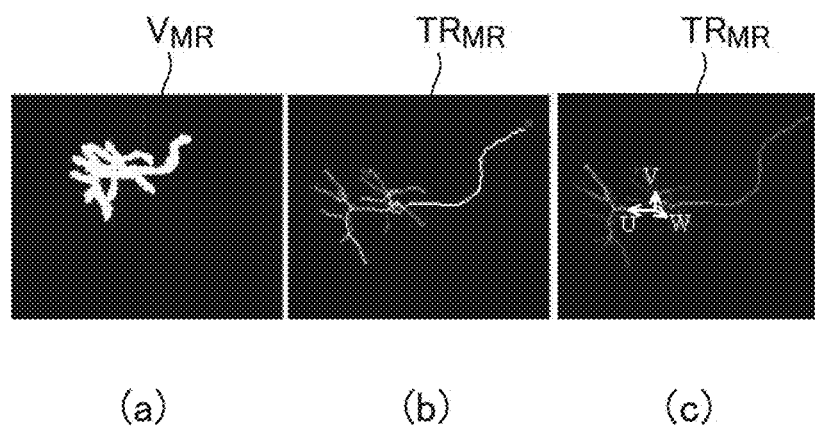
FIG. 3 is a picture showing exemplary MR vascular image, MR vascular tree, and result of calculation of vectors U, V, W at an MR vascular bifurcation.

FIG. 3(a) shows a sample of the MR vascular image $V_{MR}$ as exemplary vascular image.

The partial vascular structure detecting section 4 detects one or more partial vascular structures in each of the extracted MR vascular image $V_{MR}$ and US vascular image $V_{US}$. The term partial vascular structure as used herein refers to a structure composed of a plurality of vascular parts lying close to or joining with one another. In the example here, a vascular bifurcation is detected as the partial vascular structure. The vascular bifurcation is comprised of a vascular bifurcation point, and two vascular parts branching out from the vascular bifurcation point. Accordingly, the vascular bifurcation is identified and distinguished by a position of the vascular bifurcation point, and directions of travel and lengths of the two vascular parts branching out from the vascular bifurcation point. The partial vascular structure detecting section 4 particularly conducts the following processing.

First, the extracted MR vascular image $V_{MR}$ and US vascular image $V_{US}$ are subjected to smoothing processing. This gives vascular images having smooth borders (contours). The smoothing processing employs a 3D Gaussian filter or a 3D median filter, for example.

Next, the smoothing-processed MR vascular image $V_{MR}$ and US vascular image $V_{US}$ are subjected skeleton processing (3D thinning processing). This gives a "vascular tree"

with which only axes in the directions of travel of blood vessels are represented as lines like branches. The vascular tree obtained from the MR vascular image will be referred to hereinbelow as MR vascular tree $TR_{MR}$ and that from the US vascular image as US vascular tree $TR_{US}$. The skeleton processing is achieved using a technique disclosed in Non-patent Document: Lee et. al, "Building skeleton models via 3-D medial surface/axis thinning algorithms," Computer Vision, Graphics, and Image Processing, 56(6), 462-478, 1994, for example. FIG. 3(b) shows a sample of the MR vascular tree $TR_{MR}$ as exemplary vascular tree. In FIG. 3(b), numerals put to the vascular parts designate tag indices.

Then, one or more vascular bifurcation points are detected in each of the MR vascular tree $TR_{MR}$ and US vascular tree $TR_{US}$. Now specific processing will be described below.

Figure 4:
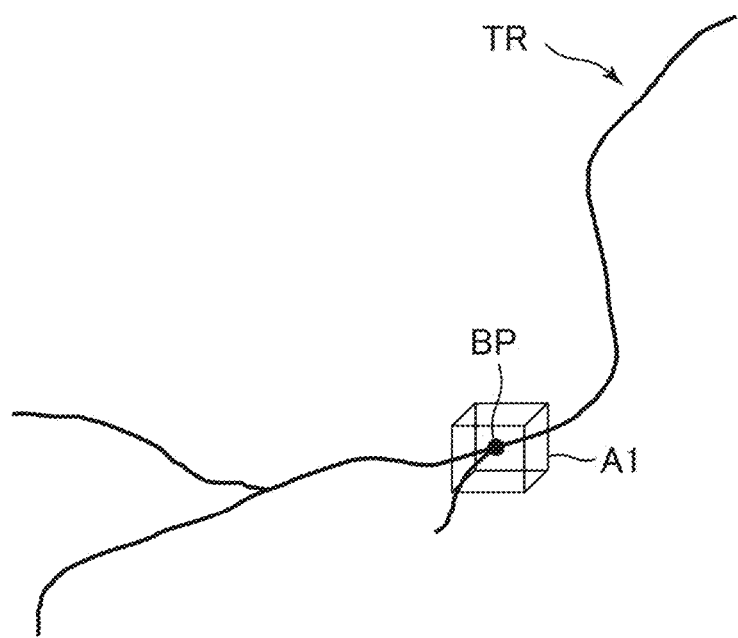
FIG. 4 is a diagram for explaining a method of detecting a vascular bifurcation point.

FIG. 4 is a diagram for explaining a method of detecting a vascular bifurcation point. As shown in FIG. 4, a region of a prespecified size containing points in branches of a vascular tree TR along the branches is defined as region to be analyzed A1. The region to be analyzed A1 is, for example, a 3D region of [3×3×3] pixels around a pixel corresponding to a point in a branch of the vascular tree TR. Then, the region to be analyzed A1 is subjected to analysis to detect contiguous pixels forming a vascular bifurcation. The analysis is started from an end of a branch corresponding to a thickest vascular part in a vascular image from which the vascular tree is derived so that the analysis is made from a trunk toward a tip of a branch in the vascular tree. Then, a point at which the contiguous pixels branch out is detected as vascular bifurcation point BP. While the vascular 'bifurcation' is typically a bifurcation in which one blood vessel branches out into two blood vessels, there may be a tri- or more furcation in which one blood vessel branches out into three or more blood vessels at an identical furcation point. The tri- or more furcation is recognized as a plurality of bifurcations. In the following description, each vascular bifurcation point detected in the MR vascular tree $TR_{MR}$ is designated as MR vascular bifurcation point $BP_{MR,i}$ (i=1, 2, . . . ), and that detected in the US vascular tree $TR_{US}$ as US vascular bifurcation point $BP_{US,j}$ (j=1, 2, . . . ).

When detecting vascular bifurcation points in the whole vascular tree, vascular bifurcation points from which vascular parts having a very small length branch out may be excluded and only those from which vascular parts having a relatively large length exceeding a prespecified threshold branch out may be detected for simplification.

Next, for each of the MR vascular bifurcation points $BP_{MR,i}$ and US vascular bifurcation points $BP_{US,j}$, two vectors corresponding to two vascular parts branching out from that vascular bifurcation point are determined. Now specific processing will be described below.

Figure 5:
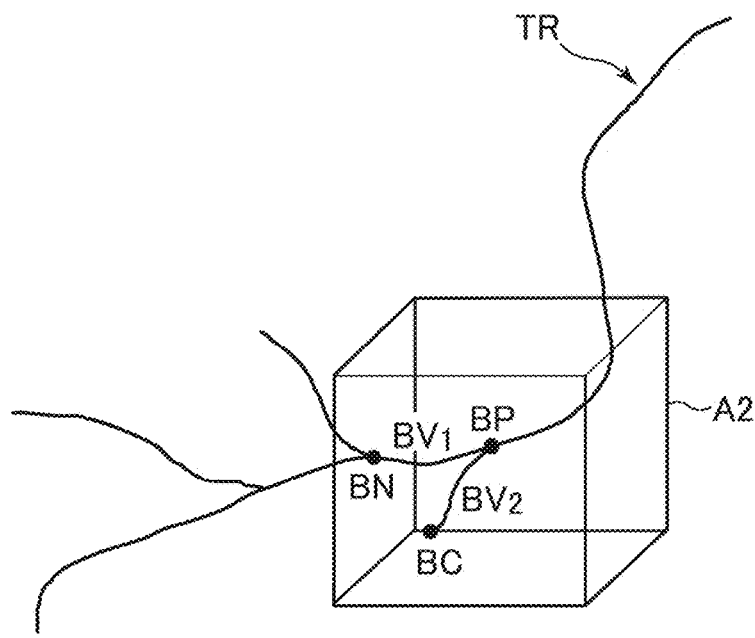
FIG. 5 is a diagram for explaining a method of determining vectors corresponding to vascular parts forming the vascular bifurcation.
Figure 5:
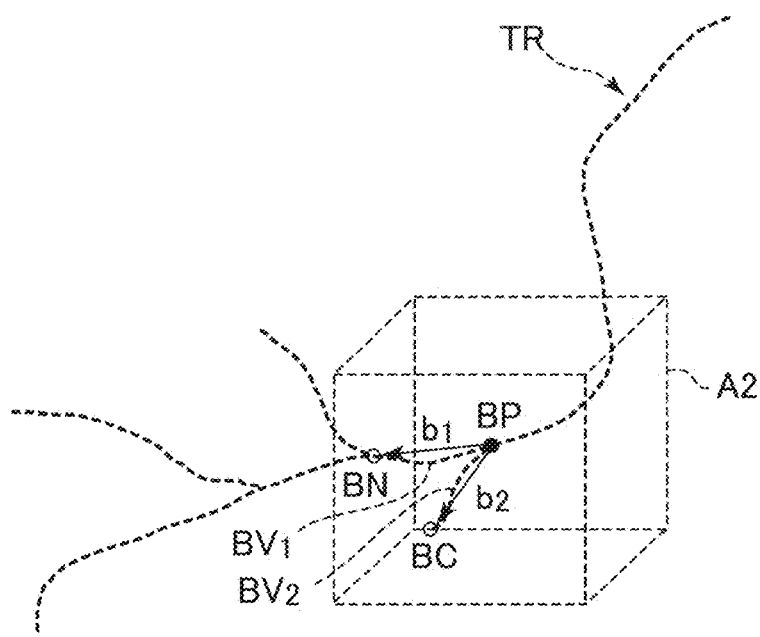

FIG. 5 is a diagram for explaining a method of determining vectors corresponding to vascular parts forming a vascular bifurcation. As shown in FIG. 5(a), for each vascular bifurcation point BP in the vascular tree TR, a region of a prespecified size containing that vascular bifurcation point BP is defined as region of interest A2. The region of interest A2 is, for example, a 3D region of [10×10×10] pixels around the vascular bifurcation point BP. The region of interest A2 includes two vascular parts $BV_1$, $BV_2$ branching out from the vascular bifurcation point BP. Next, as shown in FIG. 5(b), vectors $b_1$, $b_2$ representing the directions of travel and lengths of the two vascular parts $BV_1$, $BV_2$, respectively, are determined. In the region of interest A2, in case that a next vascular bifurcation point BN appears in a vascular part of interest branching out from the vascular bifurcation point BP, the direction of travel and length of the branching vascular part $BV_1$, $BV_2$ out from the vascular bifurcation point BP are defined as direction and length of a line segment connecting the vascular bifurcation point BP of interest and the next vascular bifurcation point BN. On the other hand, in case that a specific point BC, which is a terminal point or an intersection point with a boundary plane of the region of interest A2, appears in a vascular part branching out from the vascular bifurcation point BP of interest, the direction of travel and length are defined as direction and length of a line segment connecting the vascular bifurcation point BP of interest and specific point BC.

By such processing, a vascular bifurcation may be identified by coordinates of a pixel corresponding to a vascular bifurcation point, and two vectors corresponding to two vascular parts branching out from the vascular bifurcation point in each of the MR vascular tree $TR_{MR}$ and US vascular tree $TR_{US}$. A vascular bifurcation in the MR vascular tree $TR_{MR}$ will be referred to hereinbelow as MR vascular bifurcation, and that in the US vascular tree $TR_{US}$ as US vascular bifurcation.

The matching evaluating section 5 performs matching evaluation on vascular bifurcations for each combination of the MR and US vascular bifurcations. In the example here, the smoothing-processed MR vascular image $V_{MR}$ and smoothing-processed US vascular image $V_{US}$ are registered with each other so that the MR and US vascular bifurcations to be subjected to the matching evaluation fit over each other. Then, a degree of similarity is calculated between the registered MR vascular image $V_{MR}$ and US vascular image $V_{US}$ around the MR and US vascular bifurcations to be subjected to matching evaluation. In particular, for each combination of MR and US vascular bifurcations to be subjected to matching evaluation, the following processing is applied.

Figure 6:
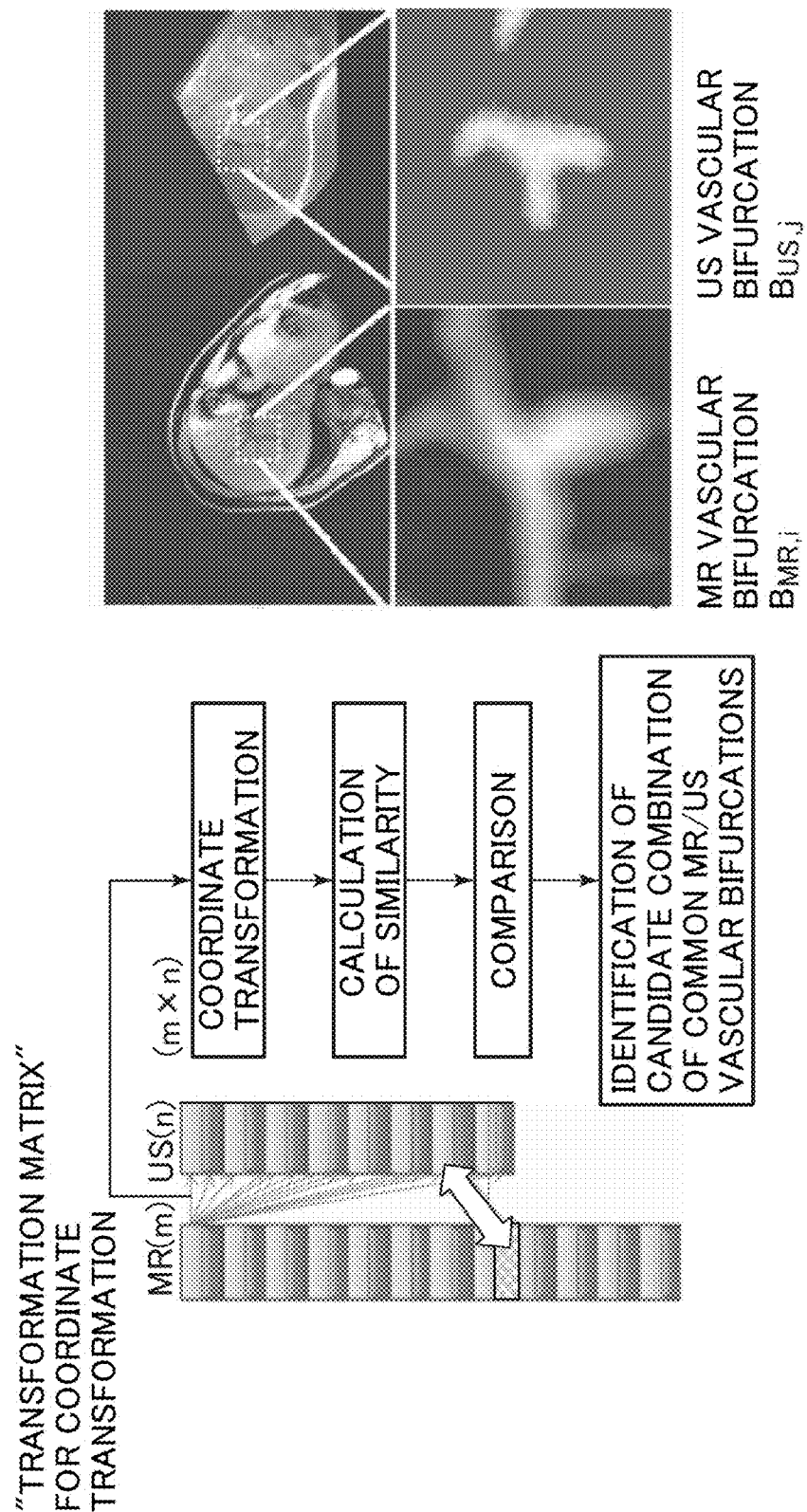
FIG. 6 is a conceptual diagram of matching evaluation for a vascular bifurcation.

FIG. 6 shows a conceptual diagram of matching evaluation for vascular bifurcations. First, the smoothing-processed MR vascular image $V_{MR}$ and US vascular image $V_{US}$ are subjected to coordinate transformation to place these vascular images in a coordinate space common to the MR and US vascular bifurcations to be subjected to matching evaluation.

The coordinate space is one defined such that an MR vascular bifurcation point in the MR vascular bifurcation to be subjected to matching evaluation and a US vascular bifurcation point in the US vascular bifurcation to be subjected to matching evaluation fit over each other, and moreover, a plane containing two vectors corresponding to two vascular parts forming the MR vascular bifurcation and that containing two vectors corresponding to two vascular parts forming the US vascular bifurcation fit over each other. The coordinate space will be referred to hereinbelow as first common coordinate space. The smoothing-processed MR vascular image $V_{MR}$ may be placed in the first common coordinate space by finding a transformation matrix corresponding to the MR vascular bifurcation to be subjected to matching evaluation, and using the transformation matrix to perform coordinate transformation on the MR vascular image $V_{MR}$. Likewise, the smoothing-processed US vascular image $V_{US}$ may be placed in the first common coordinate space by finding a transformation matrix corresponding to the US vascular bifurcation to be subjected to matching evaluation, and using the transformation matrix to perform coordinate transformation on the US vascular image $V_{US}$.

Figure 7:
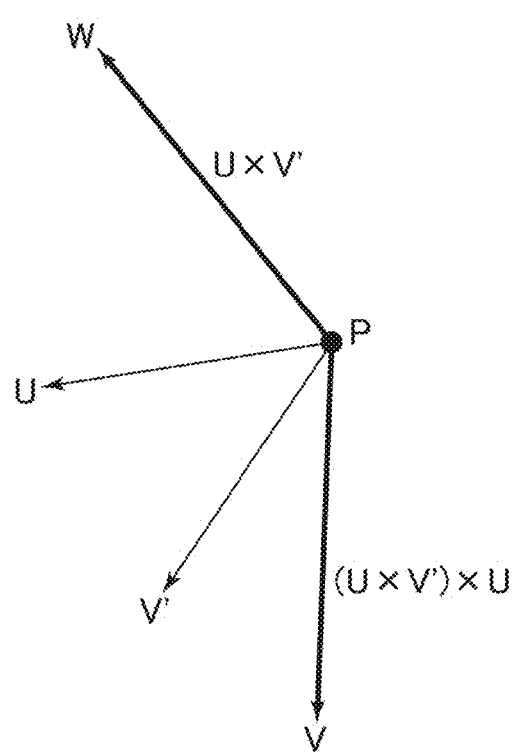
FIG. 7 is a diagram for explaining vectors defining a vascular bifurcation.

Now a method of finding a transformation matrix will be described. The transformation matrix is comprised of an origin at a center of the first common coordinate space, and a rotation matrix defining an attitude (orientation) of the vascular bifurcation. As shown in FIG. 7, let us represent the vascular bifurcation point by P=[$p_x$, $p_y$, $p_z$], vectors corresponding to the vascular parts branching out from the vascular bifurcation point P by U and V', and a vector perpendicular to a UV' plane, i.e., a normal vector, by W. A vector perpendicular to a WU plane is represented by V. Then, the mutually orthogonal vectors U, V, W are determined by the attitude of the vascular bifurcation at issue to define a rotation matrix. FIG. 3(c) shows a sample of a result of calculation of the vectors U, V, W at an MR vascular bifurcation.

$$U=[u_x,u_y,u_z], \quad V'=[v'_x,v'_y,v'_z]$$

$$W=U\times V'=[w_x,w_y,w_z]$$

$$V=(U\times V')\times U=[v_x,v_y,v_z]$$

The transformation matrix is determined for each of MR vascular bifurcations detected in the MR vascular tree $TR_{MR}$ and US vascular bifurcations detected in the US vascular tree $TR_{US}$. A transformation matrix $T_{MR-BF}$ determined for an MR vascular bifurcation and a transformation matrix $T_{US-BF}$ determined for a US vascular bifurcation may be represented as follows:

$$T_{MR-BF} = \begin{bmatrix} u_x & u_y & u_z & p_x \\ v_x & v_y & v_x & p_y \\ w_x & w_y & w_z & p_z \\ 0 & 0 & 0 & 1 \end{bmatrix}_{MR} \quad \text{[Equation Image 1]}$$

$$T_{US-BF} = \begin{bmatrix} u_x & u_y & u_z & p_x \\ v_x & v_y & v_x & p_y \\ w_x & w_y & w_z & p_z \\ 0 & 0 & 0 & 1 \end{bmatrix}_{US}$$

In case that scaling is differently set between the 3D MR image $G_{MR}$ and 3D US image $G_{US}$, a corresponding transformation matrix for the MR or US vascular bifurcation may be multiplied by a scaling ratio 'scal' to balance out the difference in scaling. A scaling ratio matrix between the 3D MR image $G_{MR}$ and 3D US image $G_{US}$ may be represented as follows:

$$scal = \begin{bmatrix} f_x & 0 & 0 & 0 \\ 0 & f_y & v_z & 0 \\ 0 & 0 & f_z & 0 \\ 0 & 0 & 0 & 1 \end{bmatrix} \quad \text{[Equation Image 2]}$$

In this matrix, scaling parameters fx, fy, fz may be determined from the scaling ratio in a corresponding real space between the 3D MR image $G_{MR}$ and 3D US image $G_{US}$.

Once the smoothing-processed MR vascular image $V_{MR}$ and US vascular image $V_{US}$ have been placed in the first common coordinate space, a degree of similarity between the MR vascular image $V_{MR}$ and US vascular image $V_{US}$ is calculated. In particular, in the first common coordinate space, a region of a prespecified size containing the origin of the first common coordinate space is defined as region to be evaluated for each of the MR vascular image $V_{MR}$ and US vascular image $V_{US}$. The region to be evaluated is, for example, a 3D region of [64×64×64] pixels around the origin. Then, a degree of similarity in the region to be evaluated is calculated between the MR vascular image $V_{MR}$ and US vascular image $V_{US}$. The degree of similarity used is, for example, a cross-correlation coefficient. A correlation function for use in calculation of the cross-correlation coefficient may be any known one.

Such coordinate transformation of the MR and US vascular images into the first common coordinate space and calculation of a degree of similarity are performed for each combination of MR and US vascular bifurcations. Specifically, representing the number of MR vascular bifurcations as m and that of US vascular bifurcations as n, transformation matrices for m MR vascular bifurcations and those for n US vascular bifurcations may be represented as follows:

$$\{T_{1MR-BF}, T_{2MR-BF}, \ldots, T_{mMR-BF}\} \{T_{1US-BF}, T_{2US-BF}, \ldots, T_{nUS-BF}\}$$

Then, the matching evaluation processing described above is conducted for a number of combinations of MR and US vascular bifurcations, i.e., m×n. However, which one of the vascular parts constituting an MR vascular bifurcation and which one of the vascular parts constituting a US vascular bifurcation are likely to be the same common blood vessel is not obvious until matching evaluation is applied. Accordingly, in practice, for each combination of MR and US vascular bifurcations, matching evaluation should be applied to a case in which, for an MR or US vascular bifurcation, the two vascular parts forming that vascular bifurcation are exchanged in position with the other. Therefore, strictly, the matching evaluation processing is conducted a number m×n×2 of times.

The matching evaluating section 5 further identifies a combination of MR and US vascular bifurcations for which a degree of similarity at a certain level or higher is calculated as candidate combination representing an identical vascular bifurcation common to the 3D MR image $G_{MR}$ and 3D US image $G_{US}$. For example, a certain number of outranking combinations of MR and US vascular bifurcations in a descending order of the degree of similarity, or combinations of MR and US vascular bifurcations for which the degree of similarity is equal to or greater than a prespecified threshold are identified as candidates.

The slice-to-be-processed identifying section 16 identifies, for each combination of vascular bifurcations identified as candidate described above, a slice containing the MR vascular bifurcation constituting the combination in the 3D MR image $G_{MR}$, and that containing the US vascular bifurcation constituting the combination in the 3D US image $G_{US}$. Here, a slice containing the MR vascular bifurcation in the 3D MR image $G_{MR}$ will be referred to as MR slice $SL_{MR}$, and a slice containing the US vascular bifurcation in the 3D US image $G_{US}$ as US slice $SL_{US}$. The MR slice $SL_{MR}$ has a slice plane parallel to a plane containing two vectors corresponding to two vascular parts forming the MR vascular bifurcation. Likewise, the US slice $SL_{US}$ has a slice plane parallel to a plane containing two vectors corresponding to two vascular parts forming the US vascular bifurcation.

The slice-to-be-processed identifying section 16 identifies, for each candidate combination, an MR slice $SL_{MR}$ and a US slice $SL_{US}$ constituting the combination as slices to be processed in sequence.

The wider-slice region projecting section 17 defines an MR wider-slice region $WR_{MR}$ in the 3D MR image $G_{MR}$ by a region including the MR slice $SL_{MR}$ to be processed and wider than the slice width of the MR slice $SL_{MR}$ in its slice axis direction. Likewise, it defines a US wider-slice region $WR_{US}$ in the 3D US image $G_{US}$ by a region including the US slice $SL_{US}$ to be processed and wider than the slice width of the US slice $SL_{US}$ in its slice axis direction.

Figure 8:
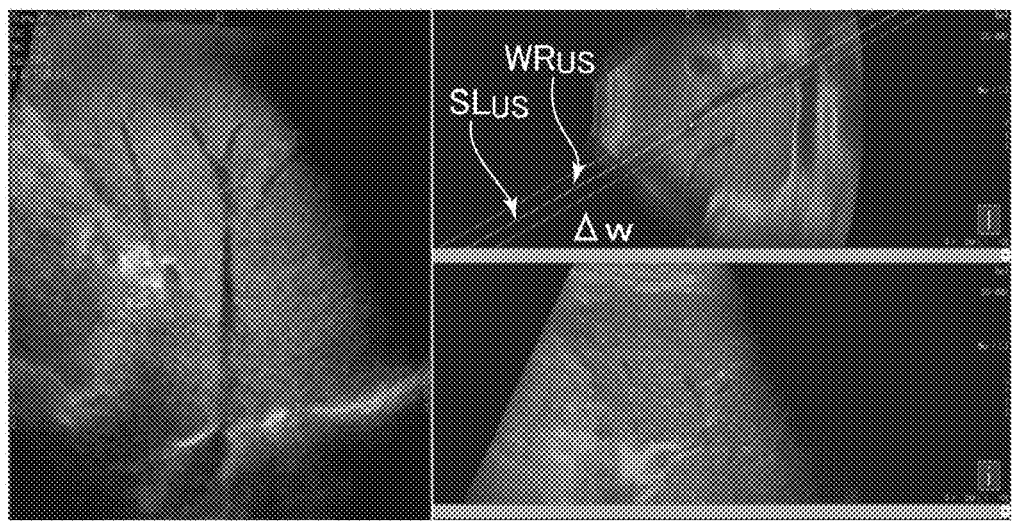
FIG. 8 is a picture showing exemplary definition of a US (UltraSound) wider-slice region including a US bifurcation slice.

FIG. 8 shows exemplary definition of a US wider-slice region including a US slice. The example here illustrates a condition in a 3D US image $G_{US}$ in which a US wider-slice region $WR_{US}$ is defined sandwiching a US slice $SL_{US}$ and having a thickness $\Delta w$ in a slice axis direction of the US slice.

The wider-slice region projecting section 17 further applies projection processing to pixel values in the MR wider-slice region $WR_{MR}$ in a slice axis direction of the MR slice $SL_{MR}$ to provide an MR wider-slice projection image $GP_{MR}$. Likewise, it applies projection processing to pixel values in the US wider-slice region $WR_{US}$ in a slice axis direction of the US slice $SL_{US}$ to provide a US wider-slice projection image $GP_{US}$.

Types of the projection processing may include, for example, maximum intensity projection (MIP) processing, minimum intensity projection (MinIP) processing, or average (or mean) intensity projection (AIP) processing. Now maximum intensity projection processing and minimum intensity projection processing on pixel values will be briefly described below.

Figure 9:
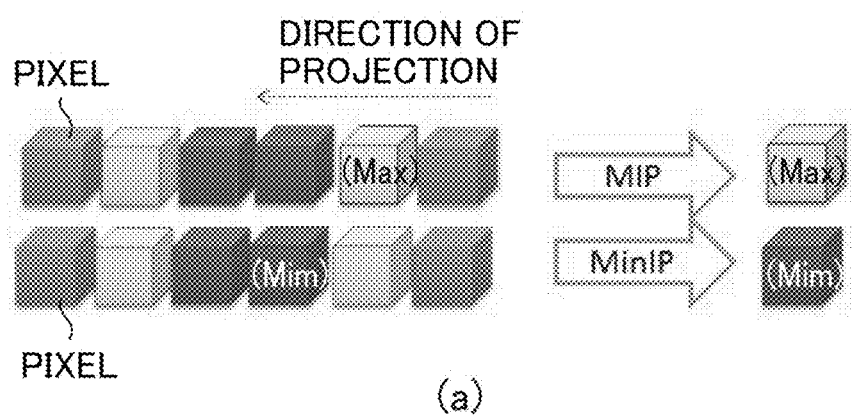
FIG. 9 is a picture showing a concept of maximum intensity projection processing and minimum intensity projection processing on pixel values.
Figure 9:
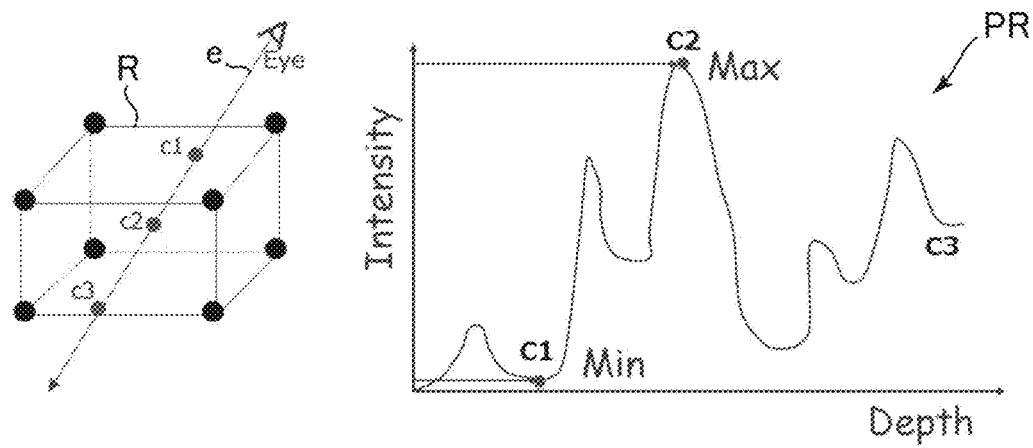

FIG. 9 is a diagram showing the concept of maximum intensity projection processing and minimum intensity projection processing on pixel values. As shown in FIG. 9(a), maximum intensity projection (MIP) processing on pixel values involves projecting a maximum one of pixel values of pixels lining up in a direction of projection in a region to be projected. Minimum intensity projection (MinIP) processing on pixel values involves projecting a minimum one of pixel values of pixels lining up in the direction of projection in the region to be projected. Now let us consider a case in which a region to be projected R is projected in a direction indicated by arrow e, as shown in FIG. 9(b). Moreover, assume that a profile of pixel values along arrow e is a profile PR as shown in FIG. 9(c), for example. In this case, maximum intensity projection processing on pixel values along arrow e causes a maximum pixel value corresponding to point c2 in the profile PR to be projected. On the other hand, minimum intensity projection processing on pixel values along arrow e causes a minimum pixel value corresponding to point c1 in the profile PR to be projected.

The type of projection processing executed by the wider-slice region projecting section 17 is determined according to by what pixel value a blood vessel is rendered in an image to be processed, that is, according to the imaging modality for the image to be processed, the type of the region to be imaged, whether a contrast medium is injected into the blood vessel or not, etc.

Now a method of determining a type of projection processing will be briefly described.

Figure 10:
FIG. 10 is a picture showing an exemplary contrast-enhanced CT (Computed Tomography) image representing a liver to which a contrast medium is injected and an exemplary contrast-enhanced MR (Magnetic Resonance) image representing the liver to which the contrast medium is injected.
Figure 10:
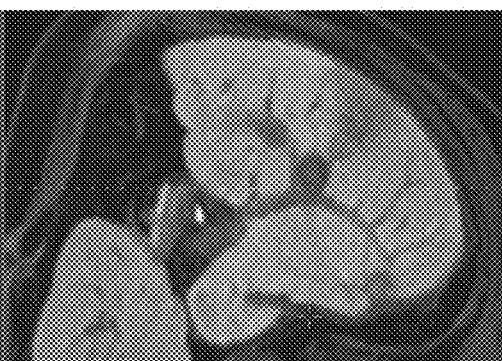

FIG. 10 shows exemplary tomographic images. FIG. 10(a) is a tomographic image corresponding to a prespecified CT slice in a 3D CT image representing a liver of a subject into which a contrast medium is injected. FIG. 10(b) is a tomographic image corresponding to a prespecified MR slice in a 3D MR image representing the liver of the subject into which the contrast medium is injected. For example, in case that a blood vessel is rendered by a higher pixel value (brightness value) than an average pixel value of its surrounding tissue, such as in the CT image representing the liver of the subject into which the contrast medium is injected as shown in FIG. 10(a), the type of projection processing used is maximum intensity projection processing. On the other hand, in case that the blood vessel is represented by a lower pixel value (brightness value) than the average pixel value of its surrounding tissue, such as in the MR image representing the liver of the subject into which the contrast medium is injected as shown in FIG. 10(b), the type of projection processing used is minimum intensity projection processing.

Figure 11:
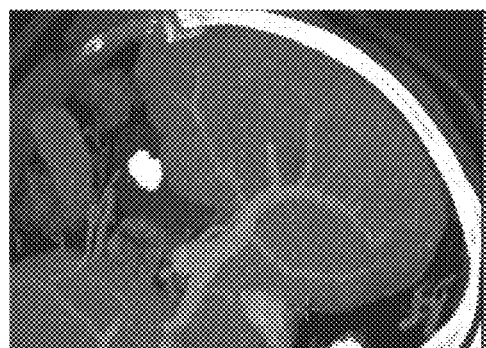
FIG. 11 is a picture showing exemplary tomographic images representing MR and US slices, respectively.
Figure 11:
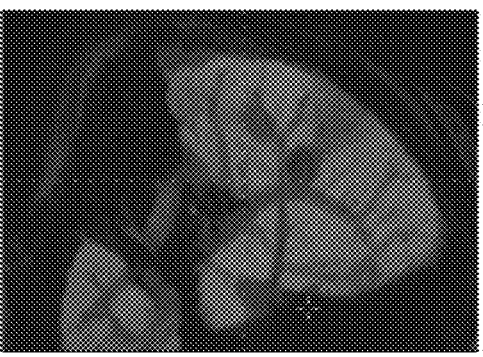

FIG. 11 shows exemplary projection images. FIG. 11(a) is a projection image obtained by applying maximum intensity projection processing to a prespecified CT wider-slice region in the 3D CT image representing the liver of the subject into which the contrast medium is injected. FIG. 11(b) is a projection image obtained by applying minimum intensity projection processing to a prespecified MR wider-slice region in the 3D MR image representing the liver of the subject into which the contrast medium is injected. As can be seen from FIG. 11, in projection images, a solid (3D) vascular structure, which would be otherwise excluded in a slice having a general slice width, is properly projected.

It should be noted that preferable examples of the slice width in the real space corresponding to the MR slice $SL_{MR}$ and US slice $SL_{US}$ and the region width in the real space corresponding to the MR wider-slice region $WR_{MR}$ and US wider-slice region $WR_{US}$ vary according to the anatomical part represented by the 3D medical image to be processed, i.e., the thickness of the blood vessel or the like. For example, in case that the anatomical part is the liver or lung, the slice width in the real space corresponding to the MR slice and US slice is preferably in a range from about 0.5 mm to 3 mm, and the region width in the real space corresponding to the MR wider-slice region $WR_{MR}$ and US wider-slice region $WR_{US}$ is preferably in a range from about 5 mm to 30 mm.

By the projection images provided by such projection processing, a vascular structure which is not included in tomographic images representing an MR or US slice and which extends to its surrounding region is rendered. The operator can thus recognize a vascular bifurcation of interest, and in addition, its surrounding vascular structure by observing such projection images. Accordingly, the operator can evaluate similarity of the vascular bifurcation of interest by visually comparing these projection images with higher accuracy, and decide whether specified MR and US vascular bifurcations are an identical vascular bifurcation or not with high certainty.

Figure 12:
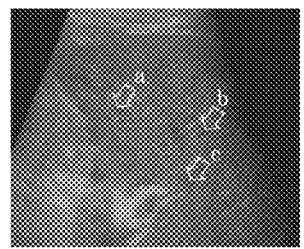
FIG. 12 is a picture showing exemplary projection images in an MR wider-slice region and in an US wider-slice region.
Figure 12:
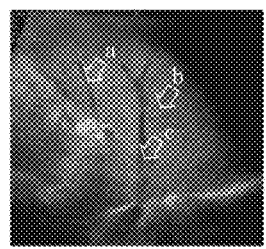
Figure 12:
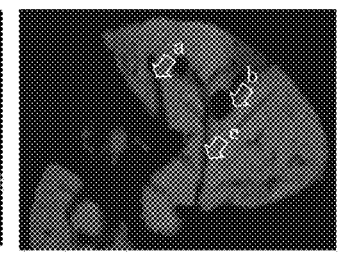

FIG. 12 shows an example of comparison between a tomographic image and a projection image. FIG. 12(a) is a tomographic image corresponding to a certain slice obtained by imaging a liver of a subject using an ultrasonic imaging apparatus in a B-mode. FIG. 12(b) is a projection image of a US wider-slice region including the slice. FIG. 12(c) is a projection image of an MR wider-slice region of a substantially and generally the same slice obtained by imaging the liver of the same subject into which a contrast medium is injected using an MR imaging apparatus. In these images, several anatomical positions are indicated by arrows with reference symbols a-c, wherein arrows with the same symbol indicate generally the same anatomical position. As can be seen from FIG. 12, it is sometimes difficult to recognize a vascular bifurcation in the ordinary tomographic image, whereas the vascular structure in the vicinity of the vascular bifurcation is properly enhanced in the projection image.

The projection image display section 18 displays MR and US wider-slice projection images for each candidate combination.

At this time, while referring to these displayed projection images, the operator chooses a combination of MR and US vascular bifurcations possibly representing an identical vascular bifurcation.

The matching fixing section 19 fixes the combination of MR and US vascular bifurcations chosen by the operator as best-matching vascular bifurcation representing an identical vascular bifurcation.

For a combination of vascular bifurcations fixed as best matching ones, the coordinate transforming section 6 determines a transformation matrix for use in coordinate transformation on the 3D MR image $G_{MR}$ based on a transformation matrix corresponding to the combination.

A transformation matrix most suitable for coarse registration is determined by the following equation:

$$T_{MR\text{-}US}=[T_{MR\text{-}BF}]_{best}[T_{US\text{-}BF}]^{-1}_{best}[\text{scal}].$$

In this equation, $[T_{MR\text{-}BF}]_{best}$ denotes a transformation matrix corresponding to a best-matching MR vascular bifurcation, and $[T_{US\text{-}BF}]^{-1}_{best}$ denotes an inverse matrix of a transformation matrix corresponding to a best-matching US vascular bifurcation.

The coordinate transforming section 6 applies coordinate transformation to the 3D MR image $G_{MR}$ using the most suitable transformation matrix $T_{MR\text{-}US}$ to coarsely register the 3D MR image $G_{MR}$ with the 3D US image $G_{US}$.

The registration adjusting section 7 applies fine registration to the coarsely registered 3D MR image $G_{MR}$ and 3D US image $G_{US}$. The fine registration is achieved using a technique of performing coordinate transformation so that pixel values, gray-scale gradients, or features such as edges match between images to be registered.

Techniques suitable for fine registration in the example here include one using a normalized gradient field (NGF), for example, Non-patent Document: Proceeding of SPIE, Vol. 7261, 72610G-1, 2009, and one disclosed in Patent Document: the specification of Japanese Patent Application No. 2013-230466. The normalized gradient field is a field obtained by, in image coordinates, calculating first-order partial differentials, i.e., gradient vectors in directions x, y, z, and then normalizing the gradient vectors by their respective lengths (vector norms). In other words, the normalized gradient field is a feature quantity representing only the directions of gradients independent of the magnitude of pixel values or brightness values, or the magnitude of gradients. In case that in two images, normalized gradient fields having the same directions are generated at positions corresponding to each other, the two images may be regarded as being registered in position. Therefore, the technique achieves registration by optimizing alignment of the directions exhibited by the normalized gradient field.

A corresponding cross-sectional image producing section 8 produces cross-sectional images corresponding to each other in the registered 3D MR image $G_{MR}$ and 3D US image $G_{US}$. The position of the cross-sectional plane of the cross-sectional image to be produced is specified by the operator, for example.

Figure 13:
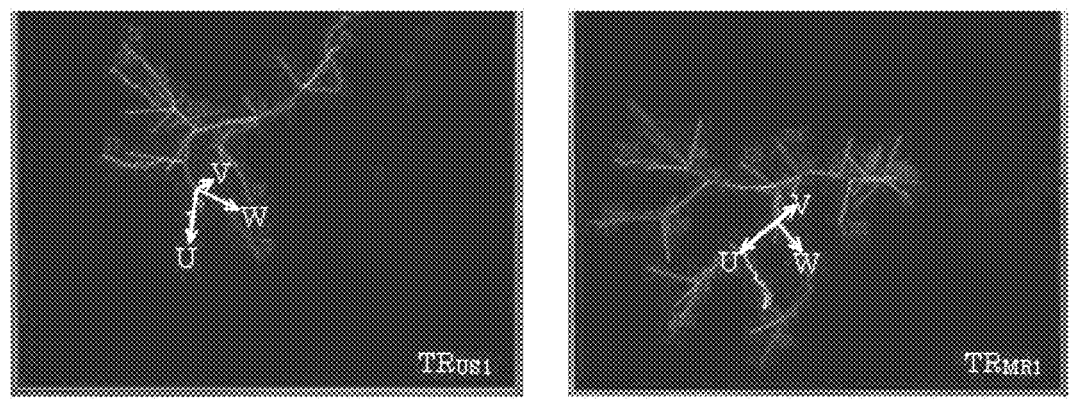
FIG. 13 is a picture showing exemplary image display.
Figure 13:
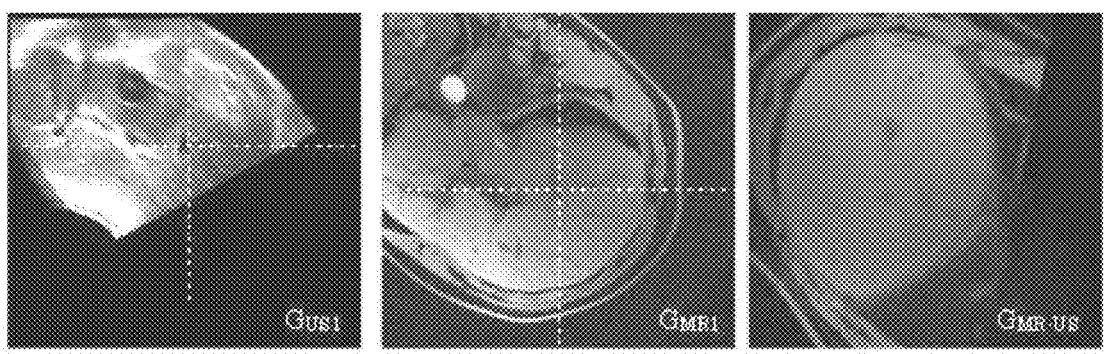

The image output section 9 displays the produced cross-sectional images on a screen, or outputs the images to the outside as image data. At that time, the best-matching combination of vascular bifurcations may be imaged and output together. For example, an MR vascular tree $TR_{MR}$ and a US vascular tree $TR_{US}$ are displayed side by side, and over these images, a vascular bifurcation point constituting a best-matching vascular bifurcation and vectors of vascular parts forming the vascular bifurcation are displayed with highlighting such as coloring. FIG. 13 shows exemplary image display. In FIG. 13, an upper-left image shows a US vascular tree $TR_{US1}$ including a result of determination of vectors U, V, W corresponding to a US vascular bifurcation for display, and an upper-right image shows an MR vascular tree $TR_{MR1}$ including a result of determination of vectors U, V, W corresponding to an MR vascular bifurcation for display. A lower-left image is a cross-sectional image $G_{US1}$ of a coordinate-transformed 3D US image in a prespecified cross section including the identified best-matching US vascular bifurcation, and a lower-central image is a cross-sectional image $G_{MR1}$ of a coordinate-transformed 3D MR image $G_{MR}$ in a prespecified cross section including the identified best-matching MR vascular bifurcation. A lower-right image is a cross-sectional image $G_{MR\text{-}US}$ of a 3D MR image $G_{MR}$ coarsely registered with a 3D US image $G_{US}$ in an arbitrary cross section.

Figure 14:
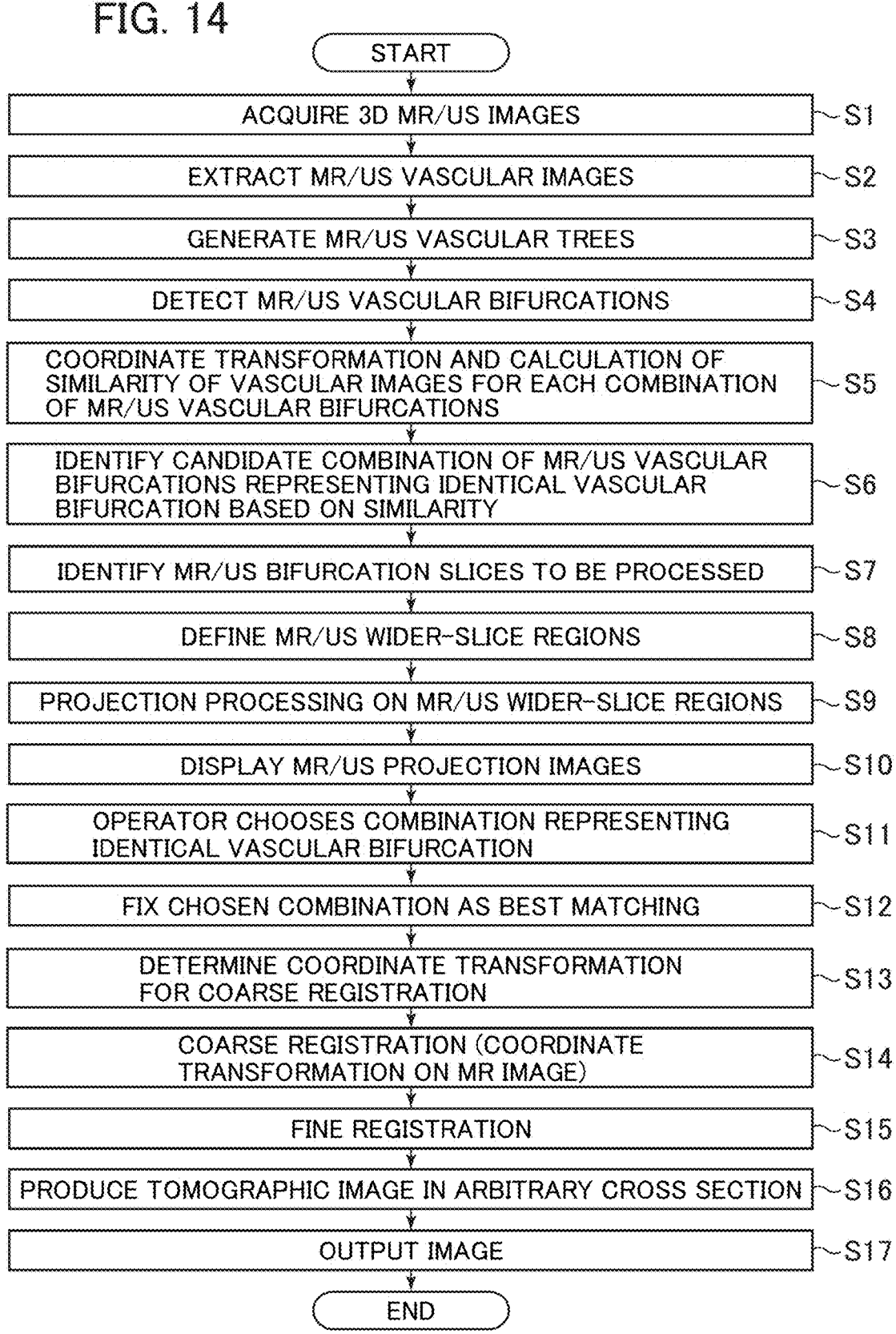
FIG. 14 is a flow chart showing flow of processing in the image processing apparatus in accordance with the first embodiment.

Now flow of processing in the image processing apparatus 1a in accordance with the first embodiment will be described. FIG. 14 is a flow chart showing the flow of processing in the image processing apparatus 1a in accordance with the first embodiment.

At Step S1, the image acquiring section 2 acquires a 3D MR image $G_{MR}$ and a 3D US image $G_{US}$ representing a liver of an identical subject. In the example here, the 3D US image $G_{US}$ is a target image and the 3D MR image $G_{MR}$ is a working image.

At Step S2, the blood vessel extracting section 3 extracts a vascular image representing a blood vessel corresponding to a hepatic portal vein or hepatic vein in each of the 3D MR image $G_{MR}$ and 3D US image $G_{US}$. The extraction is achieved by any known technique. The vascular image is extracted in a binarized image.

At Step S3, the partial vascular structure detecting section 4 applies smoothing processing and skeleton processing to each of the MR vascular image $V_{MR}$ extracted in the 3D MR image $G_{MR}$ and the US vascular image $V_{US}$ extracted in the 3D US image $G_{US}$ to provide an MR vascular tree $TR_{MR}$ and a US vascular tree $TR_{US}$.

At Step S4, the partial vascular structure detecting section 4 performs analysis on each of the MR vascular tree $TR_{MR}$ and US vascular tree $TR_{US}$ while tracking their skeletal branches. By the analysis, a position of a vascular bifurcation point and vectors corresponding to two vascular parts branching out from the vascular bifurcation point are found, whereby one or more vascular bifurcations are detected.

At Step S5, the matching evaluating section 5 registers the smoothing-processed MR vascular image $V_{MR}$ with the smoothing-processed US vascular image $V_{US}$ so that the vascular bifurcations fit over each other for each combination of MR and US vascular bifurcations to be subjected to matching evaluation. It then calculates a degree of similarity between the registered MR vascular image $V_{MR}$ and US vascular image $V_{US}$ around the MR and US vascular bifurcations of interest.

At Step S6, the matching evaluating section 5 identifies a candidate combination of MR and US vascular bifurcations representing an identical vascular bifurcation common to the 3D MR image $G_{MR}$ and 3D US image $G_{US}$ based on the calculated degree of similarity. The combination of MR and US vascular bifurcations will be referred to herein as MR/US bifurcation combination.

At Step S7, the slice-to-be-processed identifying section 16 identifies, for each MR/US bifurcation combination identified as candidate, slices to be processed by an MR slice containing an MR vascular bifurcation constituting the combination at issue in the 3D MR image $G_{MR}$ and a US slice containing a US vascular bifurcation constituting the combination at issue in the 3D US image $G_{US}$.

At Step S8, the wider-slice region projecting section 17 defines an MR wider-slice region in the 3D MR image $G_{MR}$ by a wider region including the MR slice to be processed and wider than the slice width of the MR slice in its slice axis direction. Likewise, it defines a US wider-slice region in the 3D US image $G_{US}$ by a wider region including the US slice to be processed and wider than the slice width of the US slice in its slice axis direction.

At Step S9, the wider-slice region projecting section 17 applies minimum intensity projection (MinIP) to pixel values in the MR wider-slice region in the slice axis direction of the MR slice to provide an MR wider-slice projection image. Likewise, it applies minimum intensity projection (MinIP) to pixel values in the US wider-slice region in the slice axis direction of the US slice to provide a US wider-slice projection image.

At Step S10, the projection image display section 18 displays resulting MR and US wider-slice projection images.

At Step S11, while referring to these projection images displayed, the operator chooses one of a plurality of candidate combinations of MR and US vascular bifurcations possibly representing an identical vascular bifurcation.

At Step S12, the matching fixing section 19 fixes the combination chosen by the operator as MR and US vascular bifurcations representing an identical vascular bifurcation, i.e., the best-matching combination of vascular bifurcations.

At Step S13, the coordinate transforming section 6 determines a transformation matrix $T_{MR-US}$ for use in coordinate transformation on an image for coarse registration based on a transformation matrix corresponding to the best-matching combination of vascular bifurcations.

At Step S14, the coordinate transforming section 6 applies coordinate transformation to the MR image $G_{MR}$ using the transformation matrix $T_{MR-US}$ determined at Step S7 to thereby achieve coarse registration thereof with the US image $G_{US}$.

At Step S15, the registration adjusting section 7 applies fine registration to the coarsely registered MR image $G_{MR}$ and US image $G_{US}$ for adjustment of registration. The fine registration is achieved using a technique involving applying coordinate transformation so that the pixel values, grayscale gradients, or features such as edges match between the images to be registered.

At Step S16, the corresponding cross-sectional image producing section 8 produces tomographic images in slices corresponding to each other in the registered 3D MR image $G_{MR}$ and 3D US image $G_{US}$. A slice position for the tomographic image to be processed is specified by the operator, for example.

At Step S17, the image output section 9 displays the produced tomographic images on a screen, or outputs them to the outside as image data.

An image processing apparatus 1b in accordance with the present embodiment achieves image registration even in case that only one of vascular parts branching out from a vascular bifurcation point is found in a vascular tree. In this embodiment, based on the image processing apparatus 1a according to the first embodiment, the partial vascular structure detecting section 4 and matching evaluating section 5 conducts different processing from that in the first embodiment.

Figure 15:
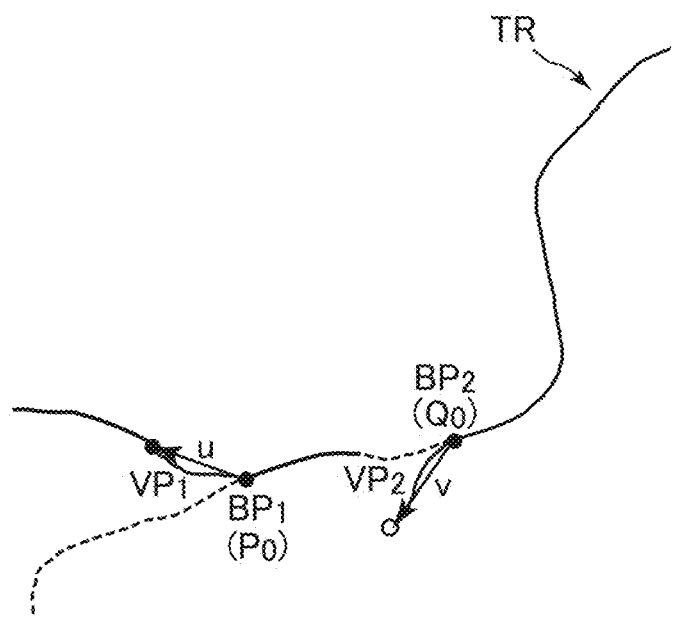
FIG. 15 is a diagram for explaining a configuration of an incomplete vascular bifurcation pair in a second embodiment.

The partial vascular structure detecting section 4 detects one or more partial vascular structures in each of the MR vascular tree $TR_{MR}$ and US vascular tree $TR_{US}$. In the example here, an incomplete vascular bifurcation pair is detected as the partial vascular structure. As shown in FIG. 15, the incomplete vascular bifurcation pair is comprised of a first vascular bifurcation point $BP_1$, one first vascular part $VP_1$ extending from the first vascular bifurcation point $BP_1$, a second vascular bifurcation point $BP_2$ proximate to but different from the first vascular bifurcation point $BP_1$, and one second vascular part $VP_2$ extending from the second vascular bifurcation point $BP_2$ in the vascular tree TR. Accordingly, the incomplete vascular bifurcation pair is identified and distinguished by a position of the first vascular bifurcation point $BP_1$, a direction of travel and a length (vector u) of the first vascular part $VP_1$ extending from the first vascular bifurcation point $BP_1$, a position of the second vascular bifurcation point $BP_2$, and a direction of travel and a length (vector v) of the second vascular part $VP_2$ extending from the second vascular bifurcation point $BP_2$.

The partial vascular structure detecting section 4 recognizes in the vascular tree a position at which a direction of extension of the blood vessel steeply changes as vascular bifurcation point, and a vascular part extending beyond the position as vascular part branching out from the bifurcation point. Thus, even in case that only one of vascular parts extending from a vascular bifurcation point is found, the vascular bifurcation point and the vascular part extending from the bifurcation point can be accurately detected.

In particular, the partial vascular structure detecting section 4 conducts the following processing.

First, in a similar manner to the first embodiment, an MR vascular tree $TR_{MR}$ and a US vascular tree $TR_{US}$ are obtained from the MR image $G_{MR}$ and US image $G_{US}$. In each of the MR vascular tree $TR_{MR}$ and US vascular tree $TR_{US}$, two or more vascular bifurcation points are detected.

Next, for each of the MR vascular bifurcation points $BP_{MR,i}$ and US vascular bifurcation points $BP_{US,j}$, one vector corresponding to one vascular part extending from the vascular bifurcation point is determined.

By such processing, in each of the MR vascular tree $TR_{MR}$ and US vascular tree $TR_{US}$, an incomplete vascular bifurcation pair may be identified by coordinates of a pixel corresponding to a first vascular bifurcation point, one vector corresponding to one first vascular part extending from the first vascular bifurcation point, coordinates of a pixel corresponding to a second vascular bifurcation point, and one vector corresponding to one second vascular part extending from the second vascular bifurcation point. The incomplete vascular bifurcation pair detected in the MR vascular tree $TR_{MR}$ will be referred to hereinbelow as MR incomplete vascular bifurcation pair, and that detected in the US vascular tree $TR_{US}$ as US incomplete vascular bifurcation pair.

The matching evaluating section 5 performs matching evaluation on the incomplete vascular bifurcation pairs for each combination of MR and US incomplete vascular bifurcation pairs. In the example here, the smoothing-processed MR vascular image $V_{MR}$ and smoothing-processed US vascular image $V_{US}$ are registered with each other so that the MR and US incomplete vascular bifurcation pairs to be subjected to matching evaluation fit over each other. A degree of similarity is calculated between the registered MR vascular image $V_{MR}$ and US vascular image $V_{US}$ around the MR and US incomplete vascular bifurcation pairs to be subjected to matching evaluation. Then, an evaluation is made that matching is better for a greater value of the degree of similarity. In particular, for each combination of the MR and US incomplete vascular bifurcation pairs to be subjected to matching evaluation, the following processing is applied.

First, the smoothing-processed MR vascular image $V_{MR}$ and US vascular image $V_{US}$ are placed in a coordinate space common to the MR and US incomplete vascular bifurcation pairs to be subjected to matching evaluation.

The coordinate space is one defined such that a specified point among the "first vascular bifurcation point," the "second vascular bifurcation point," and a "mid-point of a shortest line segment connecting a straight line extending along the first vascular part with a straight line extending along the second vascular part" in the MR incomplete vascular bifurcation pair to be subjected to matching evaluation and that specified point in the US incomplete vascular bifurcation pair to be subjected to matching evaluation fit over each other, and besides, a plane including a vector corresponding to the first vascular part and that corresponding to the second vascular part in the MR incomplete vascular bifurcation pair to be subjected to matching evaluation placed at the specified point in the MR incomplete vascular bifurcation pair and a plane including a vector corresponding to the first vascular part and that corresponding to the second vascular part in the US incomplete vascular bifurcation pair to be subjected to matching evaluation placed at the specified point in the US incomplete vascular bifurcation pair fit over each other. The coordinate space will be referred to hereinbelow as second common coordinate space.

The smoothing-processed MR vascular image $V_{MR}$ may be placed in the second common coordinate space by finding a transformation matrix corresponding to the MR incomplete vascular bifurcation pair to be subjected to matching evaluation, and using the transformation matrix to perform coordinate transformation on the MR vascular image $V_{MR}$. Likewise, the smoothing-processed US vascular image $V_{US}$ may be placed in the second common coordinate space by finding a transformation matrix corresponding to the US incomplete vascular bifurcation pair to be subjected to matching evaluation, and using the transformation matrix to perform coordinate transformation on the US vascular image $V_{US}$.

Figure 16:
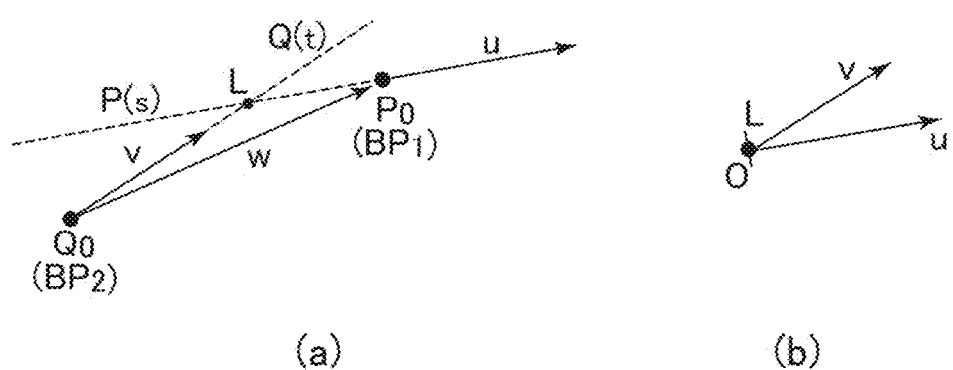
FIG. 16 is a diagram for explaining a vector defining the incomplete vascular bifurcation pair.

Now a method of finding a transformation matrix will be described. The transformation matrix is comprised of an origin at a center of the second common coordinate space, and a rotation matrix defining an attitude (orientation) of the incomplete vascular bifurcation pair. As shown in FIG. 16(a), let us represent the first vascular bifurcation point by $P_0=[p_x, p_y, p_z]$ and a vector corresponding to the first vascular part extending from the first vascular bifurcation point $P_0$ by $u=[u_x, u_y, u_z]$. Likewise, let us represent the second vascular bifurcation point by $Q_0=[q_x, q_y, q_z]$, and a vector corresponding to the second vascular part extending from the second vascular bifurcation point $Q_0$ by $v=[v_x, v_y, v_z]$. A shortest line segment connecting a straight line extending along the vector U with a straight line extending along the vector v is denoted as L. Then, the origin at the center of the second common coordinate space may be the first vascular bifurcation point $P_0$, the second vascular bifurcation point $Q_0$, or a mid-point O of the shortest line segment L, as shown in FIG. 16(b). Moreover, the vectors u and v may be moved to lie at the center, i.e., origin, of the second common coordinate space. The vectors u, v may now be operated in a similar manner to the vectors U, V' corresponding to the two vascular parts in the first embodiment. Thereafter, a similar method to that in the first embodiment may be employed to calculate a transformation matrix for coordinate transformation to the second common coordinate space from the incomplete vascular bifurcation pair.

The shortest line segment L may be determined as follows.

A formula of a line vector passing through the first vascular bifurcation point $P_0$ and extending along the vector u in 3D may be represented as follows:

$$P(s)=P_0+s \cdot u,$$

where s denotes a continuously variable parameter value.

Representing a line vector between the first vascular bifurcation point $P_0$ and second vascular bifurcation point $Q_0$ as w, $$w=P_0-Q_0,$$

so that the following formula:

$$P(s)-Q_0=w+s \cdot u$$

stands.

Likewise, the following formula:

$$Q(t)-P_0=-w+t \cdot v$$

stands. In this formula, t denotes a continuously variable parameter value.

Combining these two formulae gives:

$$(P(s)-Q(t))+(P_0-Q_0)=2 \cdot w+s \cdot u-t \cdot v$$

$$(P(s)-Q(t))+w=2 \cdot w+s \cdot u-t \cdot v. \qquad (i)$$

A line segment connecting the line vector P(s) with the line vector Q(t) is shortest when it lies normal to the line vector P(s) and line vector Q(t). Let us denote here both endpoints of the shortest line segment connecting the line vector P(s) with the line vector Q(t) as P(s1), Q(t1). Then, since a scalar product of two mutually orthogonal vectors is zero, $$u \cdot (P(s1)-Q(t1))=0.$$

Substituting EQ. (i) into this equation gives:

$$u \cdot (w+s1 \cdot u-t1 \cdot v)=0.$$

Therefore, $$s1=(u \cdot v)[s1 \cdot (u \cdot v)+v \cdot w]-u \cdot w$$

$$=s1 \cdot (u \cdot v)^2+(u \cdot v)(v \cdot w)-u \cdot w$$

$$s1=[(u \cdot v)(v \cdot w)-u \cdot w]/[1-(u \cdot v)^2].$$

Similarly, $$t1=[v \cdot w-(u \cdot v)(u \cdot w)]/[1-(u \cdot v)^2].$$

The shortest line segment L is:

$$L=P(s1)-Q(t1),$$

which may be determined from the vectors u, v, w.

Once the smoothing-processed MR vascular image $V_{MR}$ and US vascular image $V_{US}$ have been placed in the second common coordinate space, a cross-correlation coefficient is calculated between the MR vascular image $V_{MR}$ and US vascular image $V_{US}$. In particular, in the second common coordinate space, for each of the MR vascular image $V_{MR}$ and US vascular image $V_{US}$, a region of a prespecified size containing the origin of the second common coordinate space is defined as region to be evaluated. The region to be evaluated is a 3D region of [64×64×64] pixels, for example, around its origin. Then, a degree of similarity, for example, a cross-correlation coefficient, is calculated between the MR vascular image $V_{MR}$ and US vascular image $V_{US}$ in the region to be evaluated.

An image processing apparatus 1c in accordance with the present embodiment achieves image registration even in case that no vascular bifurcation point is found and only vascular parts close to each other are found in a vascular tree. In this embodiment, based on the image processing apparatus 1a according to the first embodiment, the partial vascular structure detecting section 4 and matching evaluating section 5 conducts different processing from that in the first embodiment.

Figure 17:
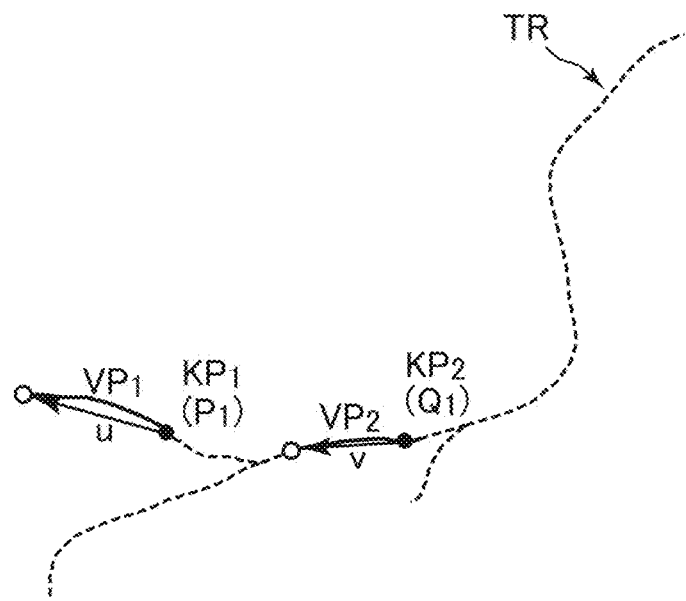
FIG. 17 is a diagram for explaining a configuration of a vascular part pair in a third embodiment.

The partial vascular structure detecting section 4 detects one or more partial vascular structures in each of the MR vascular tree $TR_{MR}$ and US vascular tree $TR_{US}$. In the example here, a vascular part pair is detected as the partial vascular structure. As shown in FIG. 17, the vascular part pair is comprised of a first vascular part $VP_1$ and a second vascular part $VP_2$ close to but different from the first vascular part $VP_1$ in the vascular tree TR. Accordingly, the vascular part pair is identified and distinguished by a position of a first vascular part endpoint $KP_1$, a direction of travel and a length (vector u) of the first vascular part $VP_1$ extending from the first vascular part endpoint $KP_1$, a position of a second vascular part endpoint $KP_2$, and a direction of travel and a length (vector v) of the second vascular part $VP_2$ extending from the second vascular part endpoint $KP_2$.

The partial vascular structure detecting section 4 recognizes a vascular part not including a vascular bifurcation point in the vascular tree, and recognizes an endpoint of the vascular part as vascular part endpoint.

In particular, the partial vascular structure detecting section 4 conducts the following processing.

First, in a similar manner to the first embodiment, an MR vascular tree $TR_{MR}$ and a US vascular tree $TR_{US}$ are obtained from the MR image $G_{MR}$ and US image $G_{US}$. Moreover, two or more mutually different vascular part endpoints are detected in each of the MR vascular tree $TR_{MR}$ and US vascular tree $TR_{US}$.

Next, for each of the MR vascular part endpoints $KP_{MR,i}$ and US vascular part endpoints $KP_{US,j}$, one vector corresponding to one vascular part extending from the vascular part endpoint is found.

By such processing, in each of the MR vascular tree $TR_{MR}$ and US vascular tree $TR_{US}$, a vascular part pair may be identified by coordinates of a pixel corresponding to the first vascular part endpoint, one vector corresponding to the one first vascular part extending from the first vascular part endpoint, coordinates of a pixel corresponding to the second vascular part endpoint, and one vector corresponding to the one second vascular part extending from the second vascular part endpoint. The vascular part pair detected in the MR vascular tree $TR_{MR}$ will be referred to hereinbelow as MR vascular part pair, and that detected in the US vascular tree $TR_{US}$ as US vascular part pair.

The matching evaluating section 5 performs matching evaluation on the vascular part pairs for each combination of MR and US vascular part pairs. In the example here, the smoothing-processed MR vascular image $V_{MR}$ and smoothing-processed US vascular image $V_{US}$ are registered with each other so that the MR and US vascular part pairs to be subjected to matching evaluation fit over each other. A degree of similarity is calculated between the registered MR vascular image $V_{MR}$ and US vascular image $V_{US}$ around the MR and US vascular part pairs to be subjected to matching evaluation. In particular, for each combination of the MR and US vascular part pairs to be subjected to matching evaluation, the following processing is applied.

First, the smoothing-processed MR vascular image $V_{MR}$ and US vascular image $V_{US}$ are placed in a coordinate space common to the MR and US vascular part pairs to be subjected to matching evaluation.

The coordinate space is one defined such that a "mid-point of a shortest line segment connecting a straight line extending along the first vascular part with a straight line extending along the second vascular part" in the MR vascular part pair to be subjected to matching evaluation and a "mid-point of a shortest line segment connecting a straight line extending along the first vascular part with a straight line extending along the second vascular part" in the US vascular part pair to be subjected to matching evaluation fit over each other, and besides, a plane including a vector corresponding to the first vascular part and a vector corresponding to the second vascular part in the MR vascular part pair to be subjected to matching evaluation placed at the mid-point of the shortest line segment in the MR vascular part pair, and a plane including a vector corresponding to the first vascular part and a vector corresponding to the second vascular part in the US vascular part pair to be subjected to matching evaluation placed at the mid-point of the shortest line segment in the US vascular part pair fit over each other. The coordinate space will be referred to hereinbelow as third common coordinate space.

The smoothing-processed MR vascular image $V_{MR}$ may be placed in the third common coordinate space by finding a transformation matrix corresponding to the MR vascular part pair to be subjected to matching evaluation, and using the transformation matrix to perform coordinate transformation on the MR vascular image $V_{MR}$. Likewise, the smoothing-processed US vascular image $V_{US}$ may be placed in the third common coordinate space by finding a transformation matrix corresponding to the US vascular part pair to be subjected to matching evaluation, and using the transformation matrix to perform coordinate transformation on the US vascular image $V_{US}$.

Figure 18:
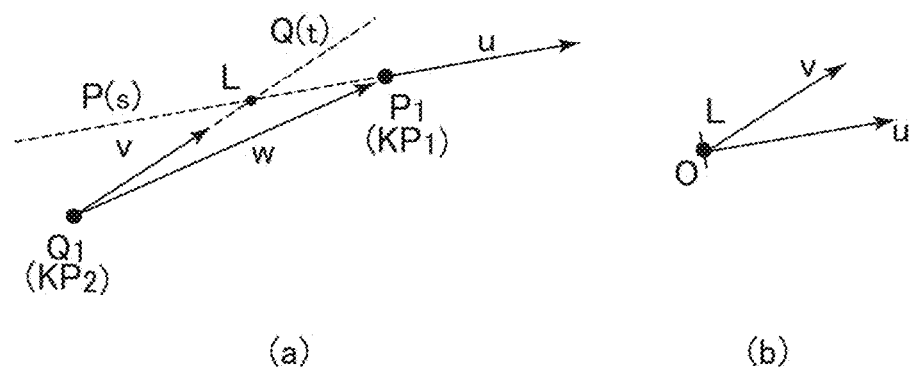
FIG. 18 is a diagram for explaining a vector defining the vascular part pair.

Now a method of finding the transformation matrix will be described. The transformation matrix is comprised of an origin at a center of the third common coordinate space, and a rotation matrix defining an attitude (orientation) of the vascular part pair. As shown in FIG. 18(a), let us represent the first vascular part endpoint by $P_1=[p_x, p_y, p_z]$, and a vector corresponding to the first vascular part extending from the first vascular part endpoint $P_1$ by $u=[u_x, u_y, u_z]$. Likewise, let us represent the second vascular part endpoint by $Q_1=[q_x, q_y, q_z]$, and a vector corresponding to the second vascular part extending from the second vascular part endpoint $Q_1$ as $v=[v_x, v_y, v_z]$. Then, a shortest line segment connecting a straight line extending along the vector u with a straight line extending along the vector v is denoted as L. Then, the origin at the center of the third common coordinate space may be a mid-point O of the shortest line segment L, as shown in FIG. 18(b). Moreover, the vectors u and v may be moved to lie at the center i.e., origin, of the third common coordinate space. The vectors u, v may now be operated in a similar manner to the vectors U, V' corresponding to the two vascular parts in the first embodiment. Thereafter, a similar method to that in the first embodiment may be employed to calculate a transformation matrix for coordinate transformation to the third common coordinate space from the vascular part pair.

Once the smoothing-processed MR vascular image $V_{MR}$ and US vascular image $V_{US}$ have been placed in the third common coordinate space, a cross-correlation coefficient is calculated between the MR vascular image $V_{MR}$ and US vascular image $V_{US}$. In particular, in the third common coordinate space, for each of the MR vascular image $V_{MR}$ and US vascular image $V_{US}$, a region of a prespecified size containing the origin of the third common coordinate space is defined as region to be evaluated. The region to be evaluated is a 3D region of [64×64×64] pixels, for example, around its origin. Then, a degree of similarity, for example, a cross-correlation coefficient, is calculated between the MR vascular image $V_{MR}$ and US vascular image $V_{US}$ in the region to be evaluated.

An image processing apparatus 1d in accordance with a fourth embodiment is for manually identifying a combination of an MR partial vascular structure (MR vascular bifurcation, MR incomplete vascular bifurcation pair, or MR vascular part pair) and a US partial vascular structure (US vascular bifurcation, US incomplete vascular bifurcation pair, or US vascular part pair) possibly representing an identical partial vascular structure (vascular bifurcation, incomplete vascular bifurcation pair, or vascular part pair).

Figure 19:
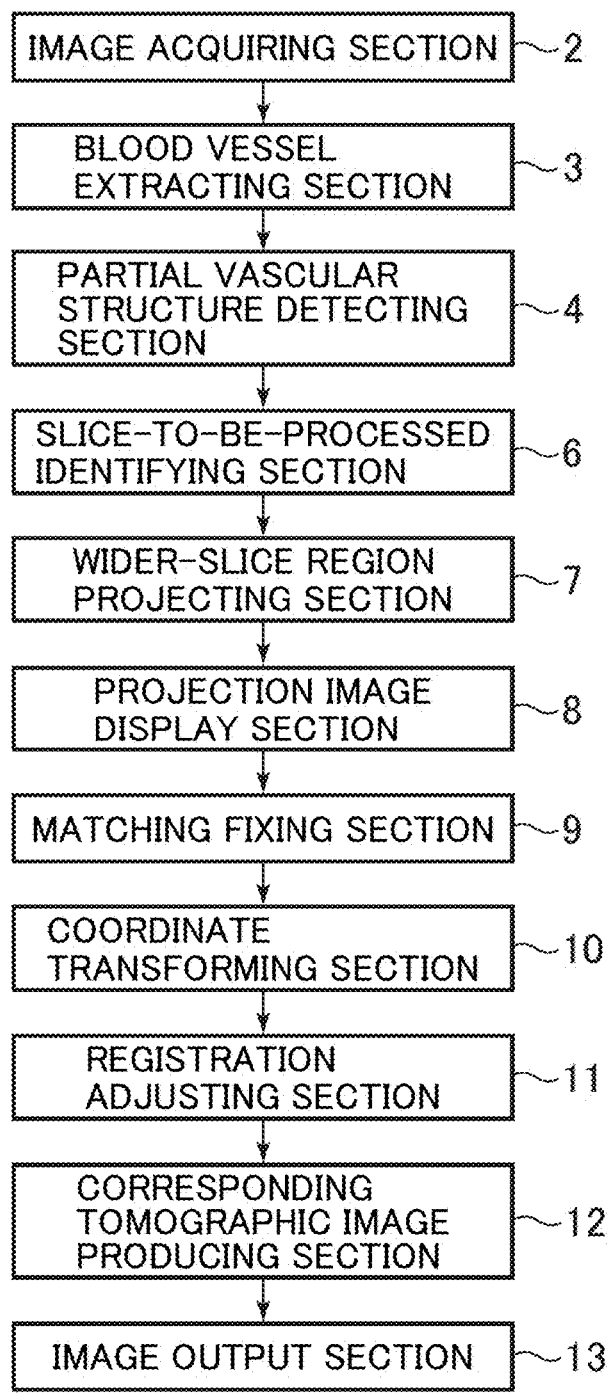
FIG. 19 is a functional block diagram schematically showing a configuration of an image processing apparatus in accordance with a fourth embodiment.

FIG. 19 is a functional block diagram schematically showing a configuration of the image processing apparatus 1d in accordance with the fourth embodiment. The image processing apparatus 1d in accordance with the fourth embodiment has a configuration based on the image processing apparatuses 1a-1c in accordance with the first-third embodiments but with the matching evaluating section 5 excluded therefrom.

In the fourth embodiment, an operator specifies a desired partial vascular structure from the detected MR partial vascular structure and US partial vascular structure.

The slice-to-be-processed identifying section 16 identifies a slice containing the MR partial vascular structure specified by the operator as MR slice $SL_{MR}$ to be processed, and a slice containing the US partial vascular structure specified by the operator as US slice $SL_{US}$ to be processed.

FIG. 20 is a flow chart showing flow of processing in the image processing apparatus 1d in accordance with the fourth embodiment. The image processing apparatus 1d in accordance with the fourth embodiment conducts processing of manually identifying a candidate at Step T5, as shown in FIG. 20, in place of the processing of automatically identifying the "candidate" at Steps S5, S6 in the first embodiment.

Thus, according to the embodiments described above, since a region including an identified slice in a 3D medical image and wider than the slice width of the slice in its slice axis direction is subjected to pixel intensity projection processing and a resulting projection image is displayed, more information on the vascular structure around the slice in the slice axis direction may be visualized without modifying the width of the slice, and the vascular structure contained in the slice may be displayed in more recognizable manner without degrading spatial resolution of the slice.

Moreover, according to the embodiments described above, an operator can confirm successful identification of a slice containing an identical partial vascular structure common to two 3D medical images to be registered or avoid false identification by referring to the displayed projection images, thus improving precision of registration. Especially in registration between two 3D medical images from mutually different imaging modalities, it is not easy to automatically identify a common identical partial vascular structure. Accordingly, displaying the projection image as in the image processing apparatuses in accordance with the embodiments above is very effective in improving precision of registration.

It should be noted that the image registration techniques according to the second and third embodiments may be performed only when complete vascular bifurcations cannot be detected or performed regardless of whether complete vascular bifurcations can be detected or not.

Moreover, while in the embodiments above, matching evaluation is performed for round-robin combinations of m partial vascular structures (vascular bifurcations, incomplete vascular bifurcation pairs, or vascular part pairs) in an MR vascular image and n partial vascular structures in a US vascular image, the present invention is not limited thereto. For example, the matching evaluation may be performed for each combination of a single one chosen by a user from among the n partial vascular structures in the US vascular image and the m vascular structures in the MR vascular image, or for each combination of a single one chosen by a user from among the m partial vascular structures in the MR vascular image and the n vascular structures in the US vascular image. The single partial vascular structure chosen by the user may be a partial vascular structure lying in the vicinity of a region of interest, for example, a tumor, in the MR or US image. By doing so, registration with particularly high precision around the region of interest may be expected, thus enabling further improvement of efficiency in diagnosis.

Further, a combination of two images subjected to registration is not limited to a combination of MR and US images, and registration may also be applied to a combination of images from any imaging modalities, such as a combination of CT and US images, or a combination of MR and CT images. However, the registration technique proposed herein achieves registration even for two images to be registered having low relevance in brightness value therebetween, almost without being affected by the low relevance. Accordingly, the registration technique proposed herein is particularly effective when a US image, which has a unique rendering mode and/or contrast, is included in images to be registered.

Furthermore, while the embodiments above refer to applications of the invention to registration of images from mutually different imaging modalities, the invention may be applied to registration of images from the same imaging modality but in mutually different temporal imaging phases. Such images may include, for example, images before and after a surgical operation, and images in early and later phases in contrast-enhanced imaging. Moreover, the invention is applicable to medical images of animals, in addition to those of human bodies.

Moreover, while the embodiments above refer to applications of the invention to processing of registration between two 3D medical images, the invention may be applied to, as another example, processing of searching for a blood vessel in a single 3D medical image. In this case, the image processing apparatus identifies a slice of interest in a single 3D medical image, applies projection processing in a slice axis direction to a region including the identified slice and wider than the width of the slice, and displays a resulting projection image. The operator can thus refer to a tomographic image of the slice of interest, such as that including a location decided to be difficult to search for, to decide whether a true blood vessel is searched for or not in the blood vessel search processing, and make adjustment so that only true blood vessels are searched for.

While a 3D medical image representing a liver of a subject is an object to be processed in the embodiments above, a 3D medical image representing a lung of a subject may be an object to be processed. Since the lung has deformability and has blood vessels as in the liver, its vascular structure may be employed as anatomical landmark. Accordingly, a 3D medical image representing the lung is suitable as an object to be processed in processing of registration between 3D medical images and/or processing of display of projection images in the embodiments above.

While the embodiments above refer to image processing apparatuses, a program for causing a computer to function as such an image processing apparatus, and a computer-readable recording medium on which the program is recorded also constitute exemplary embodiments of the invention. The recording media include non-transitory ones, in addition to transitory ones.

I claim:

1. An imaging processing method comprising:
   acquiring a first three-dimensional (3D) medical image representing an anatomical part including a blood vessel;
   acquiring a second 3D medical image representing the anatomical part;
   identifying an identical vascular bifurcation common to the first and second 3D medical images;
   identifying a first slice of interest in the first 3D medical image, wherein the first slice contains the identical vascular bifurcation and is parallel to a plane containing two vectors corresponding to two vascular parts forming the identical vascular in the first 3D medical image;
   identifying a second slice of interest in the second 3D medical image, wherein the second slice contains the identical vascular bifurcation and is parallel to a plane containing two vectors corresponding to two vascular parts forming the identical vascular in the second 3D medical image;
   applying a first projection along a slice axis direction orthogonal to the first slice of interest to generate a first projection image;
   applying a second projection along a slice axis direction orthogonal to the second slice of interest to generate a second projection image; and
   displaying the first and second projection images.

2. The method of claim 1, wherein the first 3D image is a magnetic resonance (MR) image and the second 3D image is an ultrasound (US) image.

3. The method of claim 1, wherein the anatomical part is a liver or a lung.

4. The method of claim 1, wherein the first projection is one of maximum intensity projection (MIP), minimum intensity projection (MinIP), or average intensity projection (AIP).

5. The method of claim 1, wherein applying the first projection includes applying the first projection to a region containing the first slice of interest and wider than the first slice of interest.

6. The method of claim 5, wherein a width of the first slice of interest is 3 mm or smaller in a real space and a width of the region ranges from 5 mm to 30 mm in the real space.

7. The method of claim 1, further comprising registering the first and second 3D medical images with each other based on the identical vascular bifurcation.

8. The method of claim 1, wherein identifying the identical vascular bifurcation comprises choosing one combination from a plurality of combinations of vascular bifurcations in the first 3D medical image and vascular bifurcations in the second 3D medical image.

9. A non-transitory computer readable medium storing instructions, when executed by a computer, causing the computer to:
   receive a first three-dimensional (3D) medical image representing an anatomical part including a blood vessel;
   receive a second 3D medical image representing the anatomical part;
   identify an identical vascular bifurcation common to the first and second 3D medical images;
   identify a first slice of interest in the first 3D medical image, wherein the first slice contains the identical vascular bifurcation and is parallel to a plane containing two vectors corresponding to two vascular parts forming the identical vascular in the first 3D medical image;
   identify a second slice of interest in the second 3D medical image, wherein the second slice contains the identical vascular bifurcation and is parallel to a plane containing two vectors corresponding to two vascular parts forming the identical vascular in the second 3D medical image;
   apply a first projection along a slice axis direction orthogonal to the first slice of interest to generate a first projection image;
   apply a second projection along a slice axis direction orthogonal to the second slice of interest to generate a second projection image; and
   display the first and second projection images.

10. The medium of claim 9, wherein the first 3D image is a magnetic resonance (MR) image and the second 3D image is an ultrasound (US) image.

11. The medium of claim 9, wherein the first projection is one of maximum intensity projection (MIP), minimum intensity projection (MinIP), or average intensity projection (AIP).

12. The medium of claim 9, wherein applying the first projection includes applying the first projection to a region containing the first slice of interest and wider than the first slice of interest.

13. The medium of claim 12, wherein a width of the first slice of interest is 3 mm or smaller in a real space and a width of the region ranges from 5 mm to 30 mm in the real space.

14. The medium of claim 9, further storing instructions, when executed by the computer, causing the computer to register the first and second 3D medical images with each other based on the identical vascular bifurcation.

15. The medium of claim 9, wherein identifying the identical vascular bifurcation comprises choosing one combination from a plurality of combinations of vascular bifurcations in the first 3D medical image and vascular bifurcations in the second 3D medical image.

* * * * *